US012566121B2

(12) United States Patent
Levy et al.

(10) Patent No.: US 12,566,121 B2
(45) Date of Patent: Mar. 3, 2026

(54) METHODS OF ANALYZING ONE OR MORE AGRICULTURAL MATERIALS, AND SYSTEMS THEREOF

(71) Applicant: Precision Planting LLC, Tremont, IL (US)

(72) Inventors: Kent Levy, Morton, IL (US); Reid Harman, Trivoli, IL (US); Joshua Seelye, Tremont, IL (US); Adam Vaccari, Tremont, IL (US); Riley Litwiller, Tremont, IL (US); Dale M. Koch, Tremont, IL (US)

(73) Assignee: Precision Planting LLC, Tremont, IL (US)

( * ) Notice: Subject to any disclaimer, the term of this patent is extended or adjusted under 35 U.S.C. 154(b) by 119 days.

(21) Appl. No.: 18/554,724

(22) PCT Filed: May 13, 2022

(86) PCT No.: PCT/IB2022/054456
§ 371 (c)(1),
(2) Date: Oct. 10, 2023

(87) PCT Pub. No.: WO2022/243806
PCT Pub. Date: Nov. 24, 2022

(65) Prior Publication Data
US 2024/0210375 A1 Jun. 27, 2024

Related U.S. Application Data

(60) Provisional application No. 63/191,159, filed on May 20, 2021, provisional application No. 63/191,166, (Continued)

(51) Int. Cl.
G01N 15/075 (2024.01)
G01N 1/38 (2006.01)
(Continued)

(52) U.S. Cl.
CPC ............. G01N 15/075 (2024.01); G01N 1/38 (2013.01); G01N 9/00 (2013.01); G01N 9/32 (2013.01);
(Continued)

(58) Field of Classification Search
CPC .......... G01N 15/075; G01N 1/38; G01N 9/00; G01N 9/32; G01N 27/07; G01N 27/333;
(Continued)

(56) References Cited

U.S. PATENT DOCUMENTS 3,338,171 A    8/1967   Conklin et al.
3,363,769 A    1/1968   Wilmot et al.
(Continued)

FOREIGN PATENT DOCUMENTS

EP    3636602 A1    4/2020
JP    H02191511 A    7/1990
(Continued)

OTHER PUBLICATIONS

Provolo et al: "In situ determination of slurry nutrient content by electrical conductivity", Bioresource Technology, Elsevier, Amsterdam, NL, vol. 98, No. 17, Aug. 23, 2007, pp. 3235-3242, ISSN: 0960-8524, DOI: 10.1016/J.BIORTECH.2006.07.018.

*Primary Examiner* — Roberto Velez

(57) ABSTRACT

A system may analyze agricultural materials. The system may include one or more inlets receiving the agricultural materials. The agricultural materials may be a slurry (e.g., soil slurry) including at least one solid and at least one liquid. The system may include a chamber configured to house the agricultural materials. The chamber may include a mixing device configured to mix the agricultural materials. The system may include a flow control device configured to stop the flow of the agricultural materials in a first state, or move the flow of the agricultural materials in a second state.
(Continued)

The system may include an agricultural materials density device configured to determine the density of the agricultural materials when the flow of the agricultural materials is stopped in the first state and when the flow of the agricultural materials is moving in the second state.

13 Claims, 11 Drawing Sheets

Related U.S. Application Data filed on May 20, 2021, provisional application No. 63/191,147, filed on May 20, 2021, provisional application No. 63/191,172, filed on May 20, 2021.

(51) Int. Cl.

| | | |
|---|---|---|
| *G01N 9/00* | (2006.01) | |
| *G01N 9/32* | (2006.01) | |
| *G01N 27/07* | (2006.01) | |
| *G01N 27/333* | (2006.01) | |
| *G01N 27/414* | (2006.01) | |
| *G01N 33/24* | (2006.01) | |

(52) U.S. Cl.
CPC .......... *G01N 27/07* (2013.01); *G01N 27/333* (2013.01); *G01N 27/414* (2013.01); *G01N 33/24* (2013.01); *G01N 33/245* (2024.05)

(58) Field of Classification Search
CPC .... G01N 27/414; G01N 33/24; G01N 33/245; G01N 1/08; G01N 2001/4088; G01N 2009/006
USPC ......................................................... 324/376
See application file for complete search history.

(56) References Cited

U.S. PATENT DOCUMENTS

| | | | |
|---|---|---|---|
| 3,583,209 | A | 6/1971 | Banks |
| 3,605,815 | A | 9/1971 | Von Forell |
| 4,074,562 | A | 2/1978 | North, Jr. |
| 5,332,372 | A | 7/1994 | Reynolds |
| 5,526,705 | A | 6/1996 | Skotnikov et al. |
| 5,863,443 | A | 1/1999 | Mainwaring |
| 8,325,336 | B2 | 12/2012 | Preiner et al. |
| 9,291,545 | B1 * | 3/2016 | White ...................... G01N 1/38 |
| 9,891,155 | B2 | 2/2018 | Eising |
| 2006/0219642 | A1 | 10/2006 | Farnham et al. |
| 2007/0017277 | A1 | 1/2007 | Francisco et al. |
| 2008/0053221 | A1 | 3/2008 | Allen |
| 2008/0262783 | A1 | 10/2008 | Alexander Lambert |
| 2012/0103077 | A1 * | 5/2012 | Koshnick ............... G01N 33/24 |
| | | | 73/64.56 |
| 2013/0078125 | A1 | 3/2013 | Headley et al. |
| 2015/0151223 | A1 | 6/2015 | Eckman |
| 2015/0160056 | A1 | 6/2015 | Schollenberger et al. |
| 2017/0241929 | A1 | 8/2017 | Qui et al. |
| 2018/0124992 | A1 | 5/2018 | Koch et al. |
| 2019/0120737 | A1 | 4/2019 | White et al. |
| 2021/0048424 | A1 | 2/2021 | Koshnick et al. |
| 2021/0123936 | A1 | 4/2021 | Swanson et al. |
| 2021/0208037 | A1 | 7/2021 | Swanson et al. |
| 2021/0208123 | A1 | 7/2021 | Swanson et al. |
| 2021/0269331 | A1 | 9/2021 | Anderson et al. |
| 2022/0364998 | A1 | 11/2022 | Koch et al. |
| 2023/0147351 | A1 * | 5/2023 | Machin .................... G01N 9/00 |
| | | | 73/32 R |
| 2023/0213495 | A1 | 7/2023 | Pluta |

FOREIGN PATENT DOCUMENTS

| | | |
|---|---|---|
| WO | 2000069547 A1 | 11/2000 |
| WO | 2015171908 A1 | 11/2015 |
| WO | 2021171120 A1 | 9/2021 |
| WO | 2021171121 A1 | 9/2021 |
| WO | 2021220082 A1 | 11/2021 |
| WO | 2021220083 A1 | 11/2021 |
| WO | 2021220084 A1 | 11/2021 |
| WO | 2021220085 A1 | 11/2021 |
| WO | 2022243792 A1 | 11/2022 |
| WO | 2022243793 A1 | 11/2022 |
| WO | 2022243794 A1 | 11/2022 |
| WO | 2022243795 A1 | 11/2022 |
| WO | 2022243796 A1 | 11/2022 |
| WO | 2022243797 A1 | 11/2022 |
| WO | 2022243806 A1 | 11/2022 |
| WO | 2022243807 A1 | 11/2022 |
| WO | 2022243808 A1 | 11/2022 |
| WO | 2022243809 A1 | 11/2022 |
| WO | 2022259071 A1 | 12/2022 |
| WO | 2022259073 A1 | 12/2022 |
| WO | 2022259074 A1 | 12/2022 |
| WO | 2022269388 A1 | 12/2022 |
| WO | 2023031725 A1 | 3/2023 |
| WO | 2023031726 A1 | 3/2023 |
| WO | 2023031727 A1 | 3/2023 |
| WO | 2023042036 A1 | 3/2023 |
| WO | 2023042037 A1 | 3/2023 |
| WO | 2023042038 A1 | 3/2023 |
| WO | 2023042039 A1 | 3/2023 |
| WO | 2023161727 A1 | 8/2023 |
| WO | 2023161728 A1 | 8/2023 |

\* cited by examiner

5000

5054

5052

5054

5058

5056

METHODS OF ANALYZING ONE OR MORE AGRICULTURAL MATERIALS, AND SYSTEMS THEREOF

CROSS-REFERENCE TO RELATED APPLICATIONS

The present application is a national phase entry under 35 U.S.C. § 371 of International Patent Application PCT/IB2022/054456, filed May 13, 2022, designating the United States of America and published in English as International Patent Publication WO 2022/243806 A1 on Nov. 24, 2022, which claims the benefit of priority to U.S. Provisional Application Nos. 63/191,147, 63/191,159, 63/191,166, and 63/191,172 all filed May 20, 2021. The foregoing applications are all incorporated herein by reference in their entireties.

BACKGROUND

The present disclosure relates generally to agricultural sampling and analysis, and more particularly to a fully automated system for performing soil and other types of agricultural related sampling and chemical property analysis. Periodic soil testing is an important aspect of the agricultural arts. Test results provide valuable information on the chemical makeup of the soil such as plant-available nutrients and other important properties (e.g. levels of nitrogen, magnesium, phosphorous, potassium, pH, etc.) so that various amendments may be added to the soil to maximize the quality and quantity of crop production.

In some existing soil sampling processes, collected samples are dried, ground, water is added, and then filtered to obtain a soil slurry suitable for analysis. Extractant is added to the slurry to pull out plant available nutrients. The slurry is then filtered to produce a clear solution or supernatant which is mixed with a chemical reagent for further analysis. Improvements in testing soil, vegetation, and manure are desired.

BRIEF SUMMARY

The present disclosure may be directed, in one aspect, to a system, device, or method configured to analyze agricultural materials. The system may include one or more inlets receiving the agricultural materials. The agricultural materials may include (e.g., be) a slurry (e.g., soil slurry) including at least one solid and at least one liquid. The system may include a chamber configured to house the agricultural materials. The chamber may include a mixing device configured to mix the agricultural materials. The system may include a flow control device configured to stop the flow of the agricultural materials in a first state, or move the flow of the agricultural materials in a second state. The system may include an agricultural materials density device configured to determine the density of the agricultural materials when the flow of the agricultural materials is stopped in the first state and when the flow of the agricultural materials is moving in the second state.

In another aspect, a system, device, or method may be configured to analyze agricultural materials. The system may include one or more inlets receiving the agricultural materials. The agricultural materials may include (e.g., be) a slurry (e.g., soil slurry) that includes at least one solid and at least one liquid. The system may include a chamber configured to house the agricultural materials. The chamber may include a mixing device configured to mix the agricultural materials. The system may include a particle density device configured to determine the density of the at least one solid of the agricultural materials. The system may include an agricultural materials density device (e.g., density measurement device) configured to determine the density of the agricultural materials.

In another aspect, a system, device, or method may be configured to analyze agricultural materials. The system may include one or more inlets receiving agricultural materials. The agricultural materials include (e.g., be) a slurry (e.g., soil slurry) that include at least one solid and at least one liquid. The system may include a chamber configured to house the one or more agricultural materials. The chamber may include a mixing device configured to mix the agricultural materials. The system may include a particle density device configured to determine the mass of organic matter of the at least one solid of the agricultural materials.

BRIEF DESCRIPTION OF THE DRAWINGS

The present disclosure will become more fully understood from the detailed description and the accompanying drawings, wherein.

DETAILED DESCRIPTION

Figure 1:
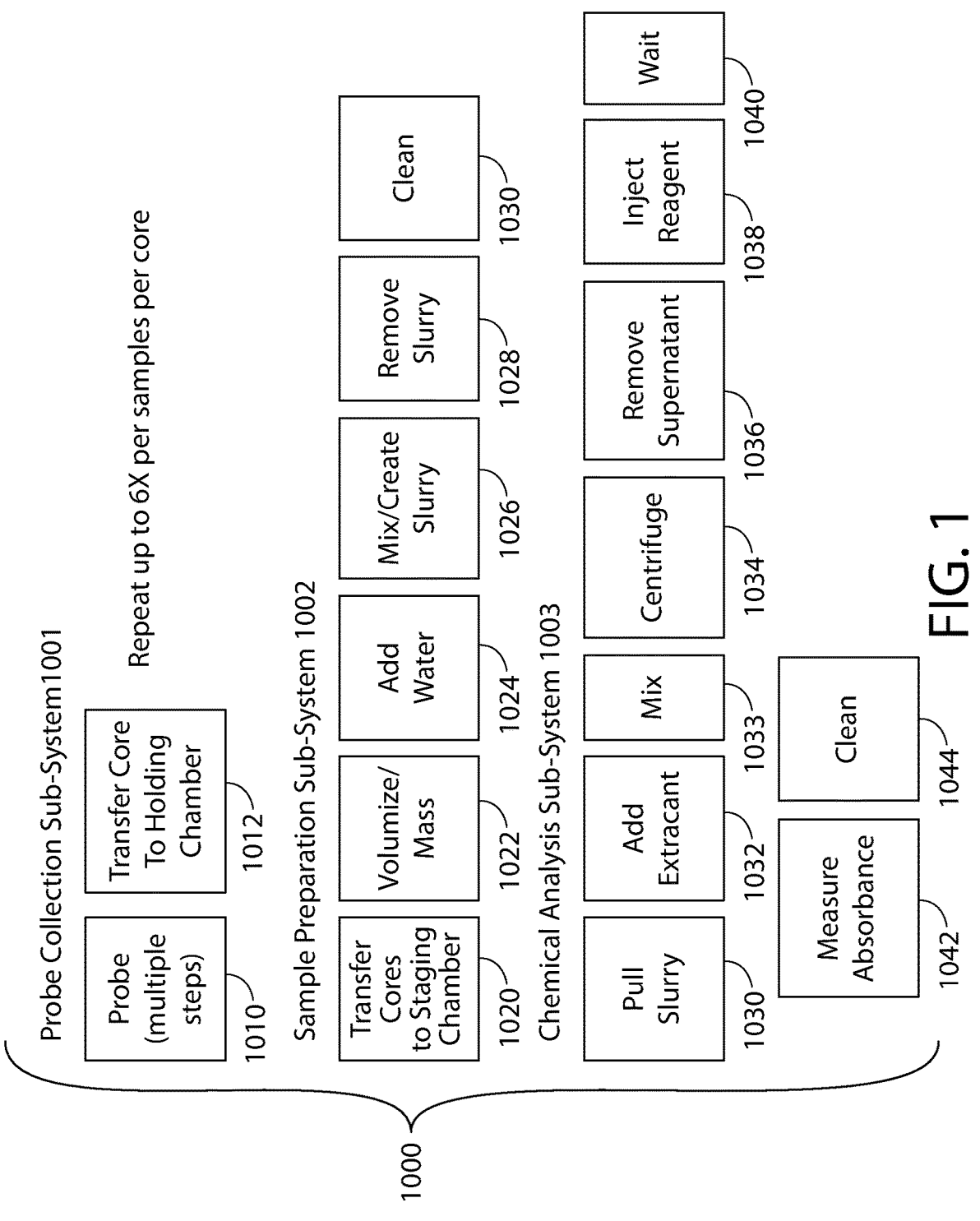
FIG. 1 is a block diagram showing aspects of sub-systems of an example sampling analysis system, as described herein.

The following description of the preferred embodiment(s) is merely exemplary in nature and is in no way intended to limit the invention or inventions. The description of illustrative embodiments is intended to be read in connection with the accompanying drawings, which are to be considered part of the entire written description. In the description of the exemplary embodiments disclosed herein, any reference to direction or orientation is merely intended for convenience of description and is not intended in any way to limit the scope of the present inventions. Relative terms such as "lower," "upper," "horizontal," "vertical," "above," "below," "up," "down," "left," "right," "top," "bottom," "front" and "rear" as well as derivatives thereof (e.g., "horizontally," "downwardly," "upwardly," etc.) should be construed to refer to the orientation as then described or as shown in the drawing under discussion. These relative terms are for convenience of description only and do not require a particular orientation unless explicitly indicated as such. Terms such as "attached," "affixed," "connected," "coupled," "interconnected," "secured" and other similar terms refer to a relationship wherein structures are secured or attached to one another either directly or indirectly through intervening structures, as well as both movable or rigid attachments or relationships, unless expressly described otherwise.

The discussion herein describes and illustrates some possible non-limiting combinations of features that may exist alone or in other combinations of features. Furthermore, as used herein, the term "or" is to be interpreted as a logical operator that results in true whenever one or more of its operands are true. Furthermore, as used herein, the phrase "based on" is to be interpreted as meaning "based at least in part on," and therefore is not limited to an interpretation of "based entirely on."

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Features of the present inventions may be implemented in software, hardware, firmware, or combinations thereof. The computer programs described herein are not limited to any particular embodiment, and may be implemented in an operating system, application program, foreground or background processes, driver, or any combination thereof. The computer programs may be executed on a single computer or server processor or multiple computer or server processors.

Processors described herein may be any central processing unit (CPU), microprocessor, micro-controller, computational, or programmable device or circuit configured for executing computer program instructions (e.g., code). Various processors may be embodied in computer and/or server hardware of any suitable type (e.g., desktop, laptop, notebook, tablets, cellular phones, etc.) and may include all the usual ancillary components necessary to form a functional data processing device including without limitation a bus, software and data storage such as volatile and non-volatile memory, input/output devices, graphical user interfaces (GUIs), removable data storage, and wired and/or wireless communication interface devices including Wi-Fi, Bluetooth, LAN, etc.

Computer-executable instructions or programs (e.g., software or code) and data described herein may be programmed into and tangibly embodied in a non-transitory computer-readable medium that is accessible to and retrievable by a respective processor as described herein which configures and directs the processor to perform the desired functions and processes by executing the instructions encoded in the medium. A device embodying a programmable processor configured to such non-transitory computer-executable instructions or programs may be referred to as a "programmable device", or "device", and multiple programmable devices in mutual communication may be referred to as a "programmable system." It should be noted that non-transitory "computer-readable medium" as described herein may include, without limitation, any suitable volatile or non-volatile memory including random access memory (RAM) and various types thereof, read-only memory (ROM) and various types thereof, USB flash memory, and magnetic or optical data storage devices (e.g., internal/external hard disks, floppy discs, magnetic tape CD-ROM, DVD-ROM, optical disk, ZIP™ drive, Blu-ray disk, and others), which may be written to and/or read by a processor operably connected to the medium.

In certain embodiments, the present inventions may be embodied in the form of computer-implemented processes and apparatuses such as processor-based data processing and communication systems or computer systems for practicing those processes. The present inventions may also be embodied in the form of software or computer program code embodied in a non-transitory computer-readable storage medium, which when loaded into and executed by the data processing and communications systems or computer systems, the computer program code segments configure the processor to create specific logic circuits configured for implementing the processes. It is noted that common components such as memory devices and power sources are not discussed herein, as their role would be easily understood by those of ordinary skill in the art.

FIG. 1 shows an example sampling system 1000. System 1000 may include one or more sub-systems that provide processing and/or chemical analysis of samples (e.g., soil samples) from collection in an agricultural field, sample preparation, and/or chemical analysis. In an example, system 1000 may be incorporated on board a motorized sampling vehicle configured to traverse an agricultural field for collecting and processing soil samples from various zones of the field. In other examples, the system 1000 may reside as a standalone station (e.g., kiosk) for processing samples.

System 1000 may provide (e.g., generate) a comprehensive and/or accurate nutrient and/or chemical profile of samples (e.g., soil samples, such as fields of soil) in order to identify (e.g., quickly and conveniently identify) soil amendments and/or application amounts necessary for one or more zones based on quantification of the plant-available nutrient and/or chemical properties in the sample. System 1000 may allow multiple samples to be processed and chemically analyzed simultaneously for various plant-available nutrients.

As provided on FIG. 1, soil sampling system 1000 may include one or more sub-systems, such as a sample probe collection sub-system 1001, sample preparation sub-system 1002, and/or chemical analysis sub-system 1003. Portions of soil sampling system 1000, including sample collection sub-system 1001, may be described in U.S. Patent Application Publication No. 2018/0124992A1, PCT Publication No. WO2020/012369, PCT Application No. PCT/IB2021/051077, filed on 10 Feb. 2021, and/or PCT Application No. PCT/IB2021/052872, filed on 7 Apr. 2021. Other sampling systems are described in U.S. Application Nos. 62/983,237, filed on 28 Feb. 2020; 63/017,789, filed on 30 Apr. 2020; 63/017,840, filed on 30 Apr. 2020; 63/018,120, filed on 30 Apr. 2020; 63/018,153, filed on 30 Apr. 2020; 63/191,147, filed on 20 May 2021; 63/191,159, filed on 20 May 2021; 63/191,166, filed on 20 May 2021; 63/191,172, filed on 20 May 2021; Ser. No. 17/326,050, filed on 20 May 2021; 63/191,186, filed on 20 May 2021; 63/191,189, filed on 20 May 2021; 63/191,195, filed on 20 May 2021; 63/191,199, filed on 20 May 2021; 63/191,204, filed on 20 May 2021; Ser. No. 17/343,434, filed on 9 Jun. 2021; 63/208,865, filed on 9 Jun. 2021; Ser. No. 17/343,536, filed on 9 Jun. 2021; 63/213,319, filed on 22 Jun. 2021; 63/260,772, filed on 31 Aug. 2021; 63/260,776, filed on 31 Aug. 2021; 63/260,777, filed on 31 Aug. 2021; 63/245,278, filed on 17 Sep. 2021; 63/264,059, filed on 15 Nov. 2021; 63/264,062, filed on 15 Nov. 2021; 63/264,065, filed on 15 Nov. 2021; 63/268,418, filed on 23 Feb. 2022; 63/268,419, filed on 23 Feb. 2022; 63/268,990, filed on 8 Mar. 2022; and PCT/IB2021/051076, filed on 10 Feb. 2021; PCT Application Nos. PCT/IB2021/051077, filed on 10 Feb. 2021; PCT/IB2021/052872, filed on 7 Apr. 2021; PCT/IB2021/052874, filed on 7 Apr. 2021; PCT/IB2021/052875, filed on 7 Apr. 2021; PCT/IB2021/052876, filed on 7 Apr. 2021. At 1010, sample collection sub-system 1001 may probe, extract, and/or collect soil samples from the field. The samples may be in the form of soil plugs, cores, and the like. At 1012, the collected samples may be transferred to a holding chamber or vessel for further processing by the sample preparation sub-system 1002.

Sample preparation sub-system 1002 may, at 1020, receive a soil sample (e.g., core) in a mixer-filter apparatus and/or transfer the cores in a staging chamber. At 1022, sample preparation sub-system 1002 may determine (e.g., quantify) the volume/mass of the soil sample. At 1024, sample preparation sub-system 1002 may add a predetermined quantity or volume of fluid, such as filtered water (e.g., based on the volume/mass of soil). At 1026, sample preparation sub-system 1002 may mix the soil and water mixture to produce a soil sample slurry. At 1028, sample preparation sub-system 1002 may remove or transfer the slurry from mixer-filter apparatus. At 1030, sample preparation sub-system 1002 may self-clean the mixer-filter apparatus. It should be understood that although soil and soil slurry are used throughout this disclosure, such terms are for illustration purposes only. The mixtures of solids and liquids may include mixtures of soil and water, as well as other mixtures including agricultural materials (e.g., manure mixtures, vegetation mixtures, etc.) in examples.

Chemical analysis sub-system 1003 may, at 1030, receive (e.g., pull) the soil slurry from a mixer-filter apparatus (e.g., a mixer-filter apparatus of sub-system 1002). At 1032, chemical analysis sub-system 1003 may add an extractant (e.g., add an extractant to the slurry). At 1033, chemical analysis sub-system 1003 may mix the extractant and slurry (e.g., in a chamber), for example, to pull out the analytes of interest (e.g. plant available nutrients). At 1034, chemical analysis sub-system 1003 may centrifuge the extractant-slurry mixture, for example, to produce a clear liquid or supernatant. At 1036, chemical analysis sub-system 1003 may remove or transfer the supernatant to a chamber (e.g., a second chamber). At 1038, chemical analysis sub-system 1003 may inject a reagent. At 1040, chemical analysis sub-system 1003 may hold the supernatant-reagent mixture for a period of hold time, for example, to allow chemical reaction (e.g., complete chemical reaction) with reagent. At 1042, chemical reaction may measure the absorbance, such as via colorimetric analysis. At 1044, chemical reaction may clean and/or assist with cleaning of the chemical analysis equipment.

Figure 2A:
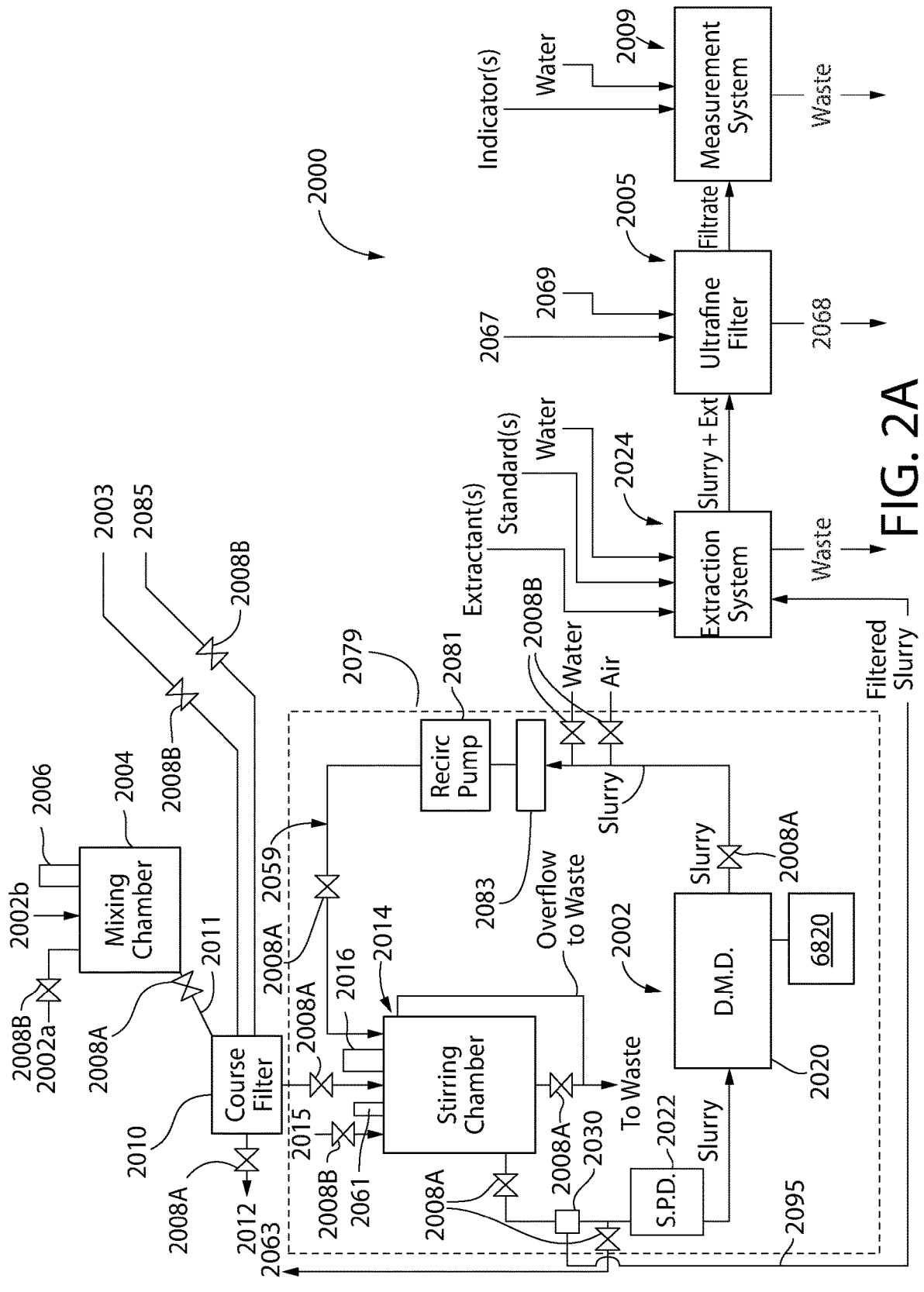
FIGS. 2A, 2B are diagrams of an example analysis system, as described herein.
Figure 2B:
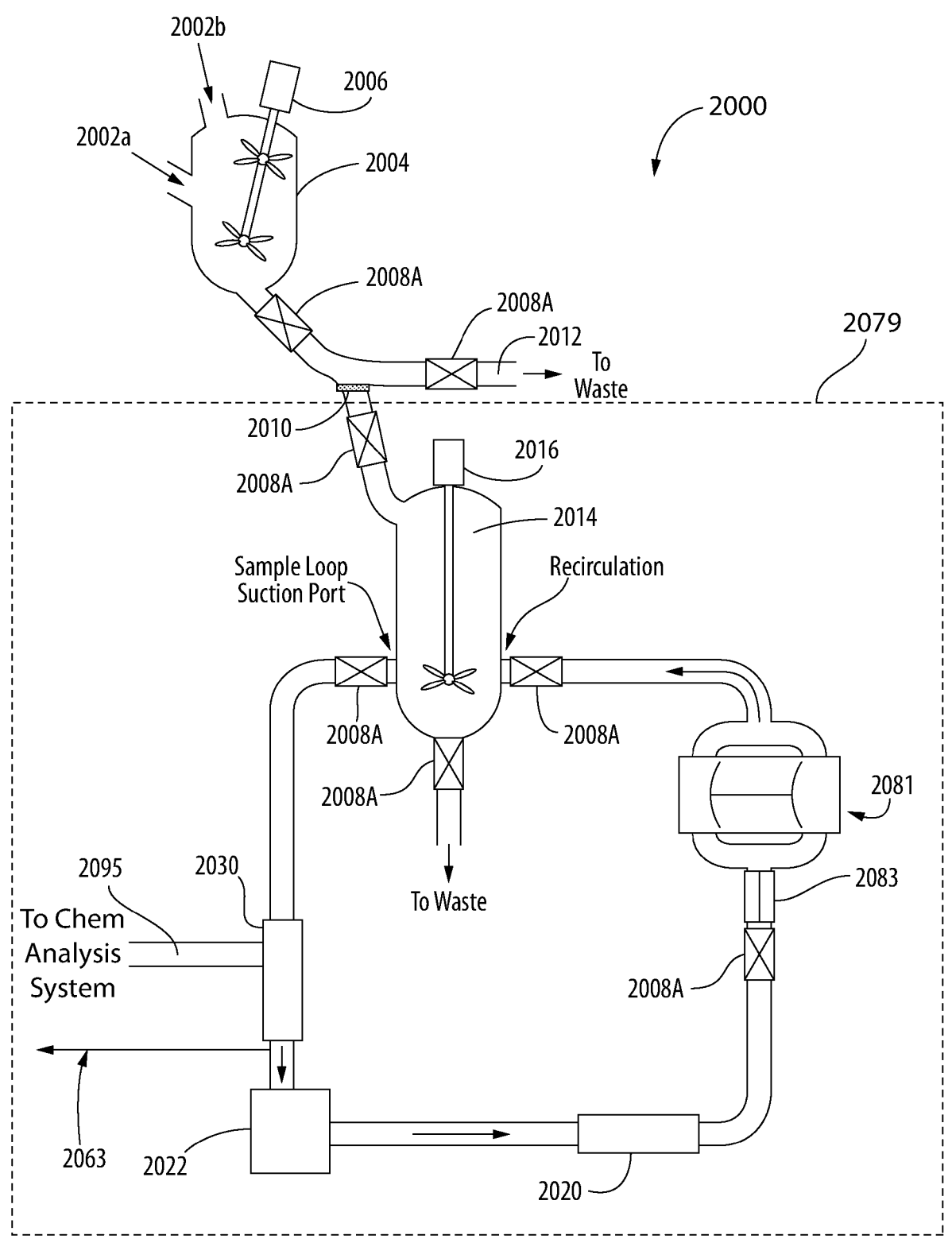

FIG. 2A is an example system diagram showing an agricultural sample analysis system 2000. FIG. 2B is an exploded view of a recirculation loop showing components within example system 2000, as shown on FIG. 2A. Agricultural sample analysis system 2000 and sampling system 1000 (FIG. 1) may have one or more (e.g., all) of the same components. It should be understood that the order of the devices and equipment shown in FIGS. 2A, 2B (e.g. pump (s), valves, etc.) is for illustration purposes only and may be switched and relocated in the systems without affecting the function of the unit. Moreover, devices and equipment such as valves, pumps, flow devices, sensors (e.g. pressure, temperature, etc.), particle density devices (e.g., soil particle density devices), density measurement devices, organic matter measurement devices, etc., may be added or removed. Accordingly, the system is not limited to the configuration and devices/equipment shown alone.

As shown on FIGS. 2A, 2B, system 2000 may include one or more inlets 2002a, 2002b (collectively inlets 2002). Inlets 2002 may provide an entryway for one or more agricultural materials, such as a solid (e.g., soil, via soil inlet 2002a), slurry (e.g., soil slurry), fluid (e.g., water) (via fluid inlet

2002b), and the like. Portions of system 2000 may represent soil sample preparation sub-system 1002 (FIG. 1), which may prepare (e.g., initially prepare) the slurry. For example, system 2000 may include one or more of a mixer, stirrer, and/or filter apparatus which may include a mixing and/or stirring chamber where water is added to a soil sample to prepare the slurry, and a coarse filter which may remove larger particles (e.g., small stone, rocks, debris, etc.) from the prepared soil slurry. The coarse filter may be sized to pass the desired (e.g., maximum) particle size in the slurry to ensure uniform flow and density of the slurry for weight/density measurement used in the process, as further described herein.

Agricultural sample analysis system 2000 may include one or more chambers (such as mixing chamber 2004 and/or stirring chamber 2014), soil particle density (S.P.D.) devices 2022, density measurement devices (D.M.D.) 2020, fine filtration devices 2030, analyte extraction systems 2024, ultrafine filtration systems 2005, and measurement systems 2009.

For example, the received agricultural material (e.g., soil) and/or a fluid (e.g., water) may be housed in a chamber, such as mixing chamber 2004. Mixing chamber 2004 may be used to combine and/or mix one or more agricultural materials. For example, as described herein, soil (e.g., soil received within soil inlet 2002a) may be mixed with a fluid (e.g., water received via fluid inlet 2002b) to produce a soil slurry. Mixing device 2006 may be used to mix, within mixing chamber 2004, the agricultural materials with a fluid. Additional material may be received by the system, such as pressured air (via inlet 2003) and/or pressured water (via inlet 2085). Mixing chamber 2004 may be configured to break down the soil and/or to ensure that the slurry is well mixed/blended. In an example, the mixing motor 2006 in the mixing chamber 2004 may run at ~15,000 rpm with one or more blades (e.g., aggressive blades). Mixing chamber 2004 may include one or more baffles (e.g., bumps) on the sidewalls. The baffles may be configured to prevent or mitigate the soil from travelling circularly along the outside of the container (e.g., to improve mixing of the materials within the slurry).

System 2000 may include one or more devices to prevent, allow, and/or reduce movement of the material (e.g., material from mixing chamber 2004). In examples, system 2000 may include one or more valves 2008A, 2008B (collectively referred to as valves 2008). Valves 2008A, 2008B (e.g., pinch valves) may prevent, allow, and/or reduce movement of the material. For example, valves 2008A may prevent, or allow, the movement of the slurry, which may include solids (e.g., soil), fluids. Valves 2008B may prevent, or allow, the movement of materials that are not the slurry, such as pressurized air and/or water to be used to unjam or clean devices of system 2000. Although FIGS. 2A, 2B show an example system 2000 having a number of valves 2008, it should be understood that more or less valves 2008 may be provided in examples.

Upon the valve(s) 2008A allowing the material (e.g., some or all of the material) to leave mixing chamber 2004, the material may move to filter 2010. The material may move to filter 2010 via mixed slurry inlet 2011. Filter 2010 may be coarse filter that permits particles that are of a desired (e.g., maximum) particle size to pass. Filter 2010 may be used to ensure that the material that passes (e.g., the material of the slurry that passes) has a uniform size. Material that does not pass (e.g., rocks or other large debris, such as wood chips and/or crop residue) through filter 2010 may be removed from system 2000 via waste output 2012.

Material that does pass through filter 2010 may move to recirculation loop 2079. Material may be held in place via valves 2008A. For example, valve 2008A may prevent material (e.g., waste) from leaving via waste output 2012 and/or valve 2008A may prevent material from being provided to recirculation loop 2079, as described herein.

Slurry recirculation loop 2079 may include a stirring chamber 2014, particle density device 2022, density measurement device 2020, and fine filtration device 2030 for particle density measurement and/or slurry density measurement (e.g., dynamic and/or continuous particle density measurement and/or slurry density measurement). One or more of the components within the slurry recirculation loop 2079 may determine a density of a slurry (e.g., total slurry density), a particle density (e.g., of the solid particles, such as soil) within the slurry, and the like. The slurry recirculation loop 2079 may be processed one or more times. In examples, the slurry recirculation loop 2079 may be processed until a desired value is achieved. For example, the slurry recirculation loop 2079 may continue to be processed until a desired ratio of a fluid (e.g., water) to solid (e.g., soil) within the slurry is achieved.

The received agricultural material (e.g., slurry, such as soil slurry) may be housed in a chamber, such as stirring chamber 2014. Stirring chamber 2014 may be used to stir one or more agricultural materials. For example, a soil slurry may be stirred with a fluid (e.g., water received via fluid inlet 2015) to produce a soil slurry with a higher ratio of fluid to soil. Stirring device 2016 may be used to stir the agricultural materials within stirring chamber 2014.

A level sensor 2061 (e.g., ultrasonic level sensor) may be provided. Level sensor 2061 may be configured to determine the fluid level of the slurry, for example, within the stirring chamber 2014. Based on the fluid level of the slurry within the stirring chamber, the level sensor 2061 may determine whether the amount of slurry within the stirring chamber 2014 is at a predetermined (e.g., desired) level. In examples, the level sensor 2061 may be configured to decrease stir speed within the stirring chamber 2014 if the fluid level within the stirring chamber 2014 is below a predefined level or increase stir speed within the stirring chamber 2014 if the fluid level within the stirring chamber 2014 is above a predefined level.

Stirring chamber 2014 may be configured to prevent soil from settling out of solution (e.g., keep the slurry in a homogenous state). In an example, the stirring motor 2016 in the stirring chamber 2014 may run one blade per shaft, for example, at ~1,000 rpm. The stirring chamber 2014 may include one or more separate shafts (e.g., two separate shafts). The shafts may be counter rotating. The one or more separate shafts may assist in stirring slurry and reducing vortexing (e.g., air that tornados down the shaft). By reducing vortexing, air may be prevented or mitigated from entering the slurry loop. Preventing or mitigating air from entering the slurry loop may improve density measurement. The slurry may tangentially be introduced into the stirring chamber 2014, for example, to reduce air entrainment.

The slurry may be filtered. For example, as shown on FIGS. 2A, 2B, the slurry may be filtered prior to the slurry moving to particle density device 2022. The slurry may be filtered prior to the slurry moving to particle density device 2022, for example, via fine filter 2030. Although FIGS. 2A, 2B show fine filter 2030 being located prior to density measurement device 2020, in examples one or more fine filters 2030 may be provided in other locations (e.g., after density measurement device 2020), or fine filter 2030 may be omitted entirely. Fine filter 2030 may include a fine screening (e.g., less than 0.04 inch/1 mm, such as about 0.010 inch/0.25 mm maximum particle size passage in one possible implementation). Fine filter 2030 may allow the agricultural slurry sample to pass through one or more analysis components without causing flow obstructions/plugging. For soil, the small particles passed by the fine filter unit may make up the majority of the nutrient content of the soil, so finely filtered slurry may be used for the ultimate chemical analysis in the system. It should be understood that the fine filtering is useable and/or applicable to slurries comprised of other agricultural materials to be sampled (e.g. vegetation, manure, etc.), and not limited to soil slurries. Particles filtered by fine filter may be discarded. For example, large particles filtered by fine filter 2030 may be discarded via waste outlet 2063.

In examples in which the slurry has not reached a desired value (e.g., desired ratio, such as a desired soil to fluid ratio), the slurry may continue to particle density device 2022 (e.g., may continue through the recirculation loop 2079, as described herein). In examples in which the slurry has reached a desired value (e.g., ratio, such as a desired soil to fluid ratio), the slurry may proceed outside of recirculation loop via outlet 2095, for example, to extraction system 2024. Although outlet 2095 is described as occurring before particle density device 2022 and density measurement device 2020, it should be understood that outlet 2095 may be positioned at any location within system 2000, such as before, between, or after particle density device 2022 and density measurement device 2020, before or after fine filter 2030, and the like.

Particle density device 2022 may be a soil particle density measurement device. As described further herein, particle density device 2022 may determine the density of a solid (e.g., soil) within the slurry. Although particle density measurement device 2022 may be described as a soil particle density measurement device 2022 throughout the disclosure, it should be understood that this is for illustration purposes only and the particle density measurement device 2022 may determine the density of one or more other agricultural solids besides soil, such as manure, vegetation, and the like. Examples of particle density devices are shown on FIGS. 4 and 5A/5B.

FIGS. 2A, 2B show density measurement device 2020. Density measurement device 2020 may determine a density of a material or a combination of materials (e.g., a slurry formed of one or more fluids and one or more solids). Density measurement device 2020 may obtain the density of the mixed agricultural sample slurry prepared in sample preparation chamber (e.g. mixer-filter apparatus). In an example, density measurement device 2020 may be a digital density meter of the U-tube oscillator type shown in FIGS. 3A-3C that may be used to measure density (e.g., overall density) of the sample slurry. Although in examples the sample slurry may be a soil slurry, the slurry may be comprised of one or more materials other than soil in other examples. For example, it should be understood that any type of agricultural sample slurry may be processed in the system, including soil, vegetation, manure, and the like. It should also be understood that the devices provided in system 2000 are for illustration purposes only. One or more devices may be added to the system 2000 or excluded by the system in examples.

The density of the soil (e.g., the soil particle density) and/or the density of the slurry (e.g., the total slurry density) may be the ratio of the mass of the soil (for soil density) and/or the mass of the slurry (for slurry density) to their respective volumes. The density of the soil (e.g., the soil particle density) and/or the density of the slurry (e.g., the total slurry density) may be used to determine the amount of diluent (e.g., water) required and/or solid (e.g., soil) to be added to a sample (e.g., a slurry sample) in order to achieve the desired water to soil ratio for chemical analysis of an analyte within the slurry, as further described herein. For example, the density of the slurry and/or the density of the solid (e.g., soil) within the slurry may be used to determine the ratio of solid (e.g., soil) to water within the slurry.

The ratio of solid to water within a slurry may be determined based on one or more parameters, such as the density of the water within the slurry, the density of the solid (e.g., soil) within the slurry, and the density of the slurry (e.g., total density of the slurry). As an example, the density of water is known. By determining the density of the solid in the slurry and the density of the slurry (e.g., total density of the slurry), the ratio of solid to water may be (e.g., accurately) determined. If the ratio of solid to water is determined, the amount of diluent (e.g., water) required to be added to the slurry (e.g., soil sample) to achieve the desired water to soil ratio may be determined. The desired water to soil ratio may be the ratio desired for chemical analysis of an analyte.

As described herein, by determining (e.g., dynamically determining) the soil particle density of the soil within the slurry, an accurate ratio of the soil to water ratio of the slurry may be determined. For example, a more accurate ratio of the soil to water ratio of the slurry may be determined over conventional systems. Thus, dynamically determining the soil particle density of the soil within the slurry provides an advantage over conventional systems, which use a predetermined (e.g., static) value for the density of the solid (e.g., soil) when determining the ratio of solid to liquid within a slurry, as the predetermined (e.g., static) value used by conventional systems for the density of the solid may not be correct or accurate.

The accuracy of the slurry density, as determined by the density measurement device 2022 (e.g., u-tube), may depend on the materials within the slurry. For example, the density measurement device 2022 may provide more accurate determinations of slurry density for homogeneous materials (e.g., material that is perfectly, or near-perfectly, mixed). A homogeneous material may be referred to as a solution in examples. In contrast, the density measurement device 2022 may provide less accurate determinations for non-homogeneous materials (not perfectly, or near-perfectly, mixed). Non-homogeneous materials may be referred to as a suspension in examples. As an example, the density measurement device 2020 may provide inaccurate (e.g., less accurate) results for a soil slurry, as the soil and the water may not perfectly (or near-perfectly mix) with one another.

To correct for non-homogeneous materials (e.g., soil slurries), the density measurement device 2022 may perform one or more actions. For example, as described herein, density measurement device 2022 may determine the total density of the slurry when the slurry is flowing through density measurement device 2022, and the density measurement device 2022 may determine the total density of the slurry when the flow of the slurry is stopped. By comparing the total density of the slurry when the slurry is flowing versus the total density of the slurry when the slurry is not flowing, a more accurate determination of total density of the slurry may be determined. For example, by not incorporating the settled particles in the total slurry density, the determined total slurry density may be comparable to determining the density of a homogeneous (e.g., more homogeneous) material.

Figure 6:
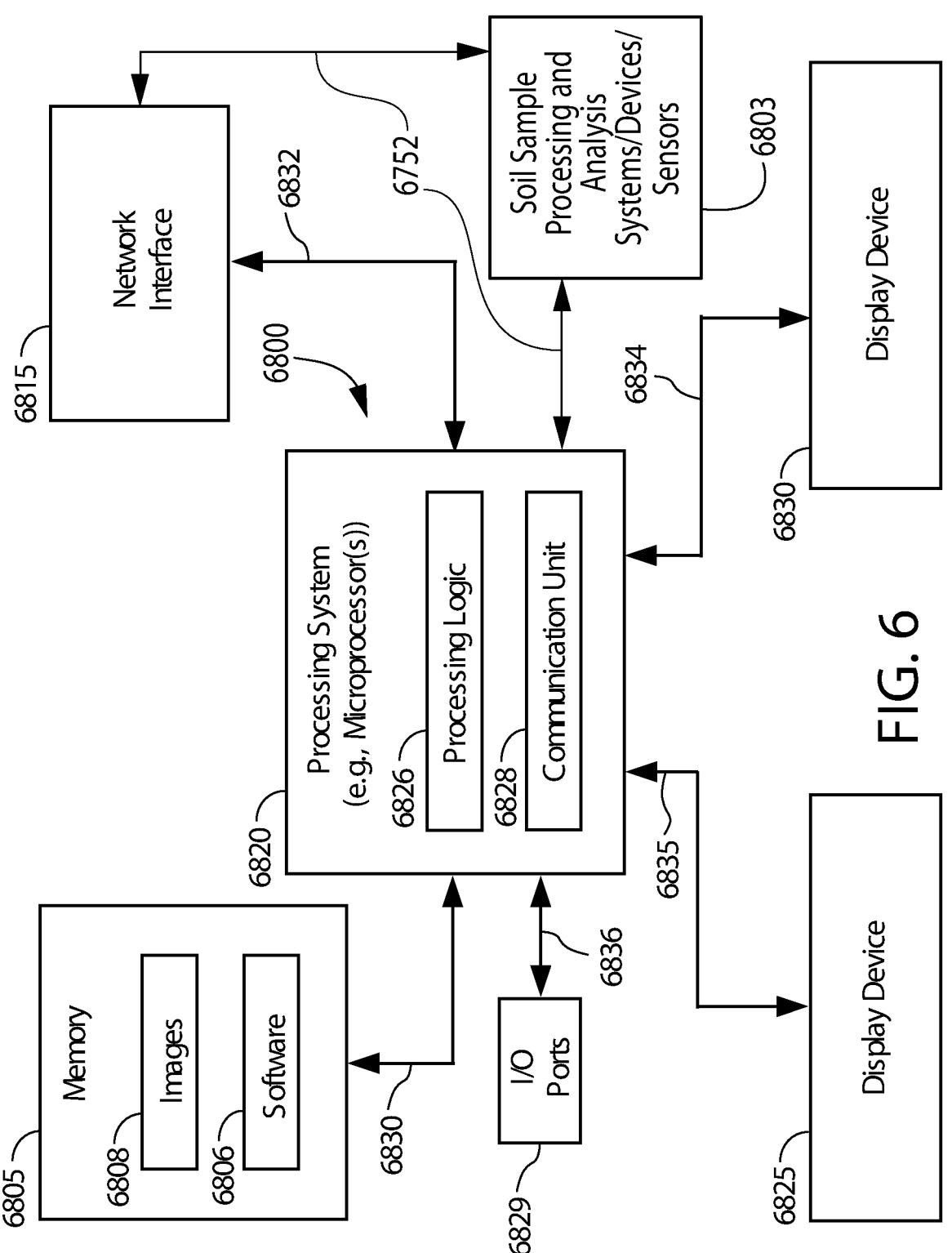
FIG. 6 shows an example controller for controlling systems and apparatuses, as described herein.

Measurements (e.g., soil particle density measurements, slurry density measurements, organic matter measures, etc.) of the slurry may be provided to system controller 6820 (also shown on FIG. 6). System controller 6820 may perform one or more operations based on the provided measurements, as described herein. For example, system controller 6820 may determine a ratio of water to soil of the slurry (e.g., the slurry passing through the recirculation loop 2079) based on the provided information. If the determined ratio is a desired ratio, system controller 6820 may cause the slurry to end (e.g., exit) the recirculation loop 2079. If the determined ratio is not a desired ratio, system controller 6820 may cause the slurry to continue the recirculation loop 2079. The slurry continuing the recirculation loop 2079 may allow additional materials (e.g., water, soil) to be added to the slurry, as described herein. For example, the slurry continuing within the recirculation loop 2079 may allow water to be added to the slurry (e.g., via fluid inlet 2015) to modify the water to soil ratio of the slurry.

In examples in which the slurry continues through the recirculation loop 2079, additional material (e.g., agricultural material) may be provided to the slurry. For example, as shown on FIGS. 2A, 2B, water and/or air may be provided. For example, water and/or air may be provided to unjam or clean one or more of the devices (e.g., tubes) in which the slurry is flowing or in which assists the slurry in flowing. The slurry may move to flow through accumulator 2083. The flow through accumulator 2083 may adjust (e.g., dampen) pressure surges and/or pulses in the recirculation loop 2079 that may be caused by recirculation pump 2081.

One or more devices may be used to assist in the flow, or to stop the flow, of the slurry through system 2000. For example, a pump, such as pump 2081 (e.g., a recirculation pump), may be used to move the slurry or stop the movement of the slurry. A valve (such as valve 2008A) may be used to allow the movement of the slurry or to prevent the movement of the slurry. For example, pump 2081 may be used to transfer the slurry from and/or to one or more mixers 2004, stirrers 2014, filter(s), density measurement devices 2020, or soil particle density device(s) 2022 via a pumping by pump 2081 and/or via pressurizing the mixer-filter apparatus chamber with pressurized air provided by a fluid coupling to a pressurized air source. In examples, pump 2081 may fluidly drive the recirculation flow in the closed recirculation flow loop 2079 formed by flow conduits 2059 (see, e.g., FIG. 2A) comprising tubing and/or piping, and return the filtered slurry back to chamber 2014. Recirculation pump 2081 may be a slurry pump. Recirculation pump 2081 may be omitted, in examples in which the slurry is capable of flowing through the closed recirculation flow loop 2079 (e.g., the entire closed recirculation flow loop 2079) absent assistance from recirculation pump 2081.

System 2000 may recirculate (e.g., continuously recirculate) the slurry (e.g., the coarsely filtered slurry) back into chamber 2014 for a period of time and/or for a number of iterations. The recirculation may assist in producing a homogeneous slurry mixture more quickly for analysis than with the mixer alone by continuously recycling the slurry through the mixer and/or coarse filter in the closed recirculation flow loop 2079. During density measurement(s), for example, fluid may be metered (e.g., automatically be metered) and/or added to a mixer-filter apparatus based on the system monitoring the slurry density measured by density measurement device 2020, which may be operably coupled to the controller in order to achieve the preprogrammed water to soil ratio. The slurry may be better mixed by this continuous slurry recirculation.

Once a homogeneous slurry (e.g., slurry having the desired water to soil ratio) is achieved, the slurry may proceed outside of recirculation loop 2079 via outlet 2095, as described herein. The slurry may proceed to extraction system 2024, ultrafine filter 2005, and/or measurement system 2009. In an example, measurement system 2009 may include one or more sensors, such as one or more ion selective electrode (ISE) or ion selective field-effect electrode (ISFET) sensors, although such examples are for illustration purposes only and the sensor may be one or more other sensors. The ISE or ISFET sensor may sense one or more analytes (e.g. P, K, Ca, Mg, etc.) when analyzing the slurry. One or more mechanisms may be provided for the cleaning (e.g., automatic cleaning) of one or more components of system 2000, such as for the cleaning of measurement system 2009. As an example, one or more ports (e.g., fluid ports) may be provided for cleaning one or more sensors of measurement system 2009. The one or more fluid ports may provide one or more fluids, such as water, to clean one or more of the sensors.

The flow of extracted slurry may be controlled by suitable control valves 2008A changeable in position between open full flow, closed no flow, and throttled partially open flows therebetween. Valves 2008 may be manually operated or automatically operated by controller to open at an appropriate time once homogenous slurry having the desired water to soil ratio has been achieved, or as otherwise preprogrammed. One or more valves 2008 may be used to open flow to water in order to backflush the filter during the cleaning cycle in preparation for the next sample.

The slurry stream may travel from the extraction system 2024 to ultrafine filtration sub-system 2005. Ultrafine filtration system 2005 may include one or more ultrafine filters configured to pass slurry particles having a size smaller than allowed to pass via course filter 2010 and fine filter 2063. For example, ultrafine filter 2005 may be a micro-porous filter which may replace centrifuge and/or may be configured to produce clear filtrate from the soil slurry and extractant mixture which serves as the supernatant for chemical analysis. In an example, representative pore sizes that may be used for ultrafine filter 2005 may be approximately 0.05 μm to 1.00 μm, although other sizes may be used. Pressurized air and fluids may be provided to slurry via pressurized air inlet 2067 and fluid inlet 2069, respectively. Waste product may be exited via waste outlet 2068. The portion of the slurry stream that passes through ultrafine filter 2005 may move to measurement system 2009, for further processing of the ratio containing the desired slurry ratio.

Figure 3A:
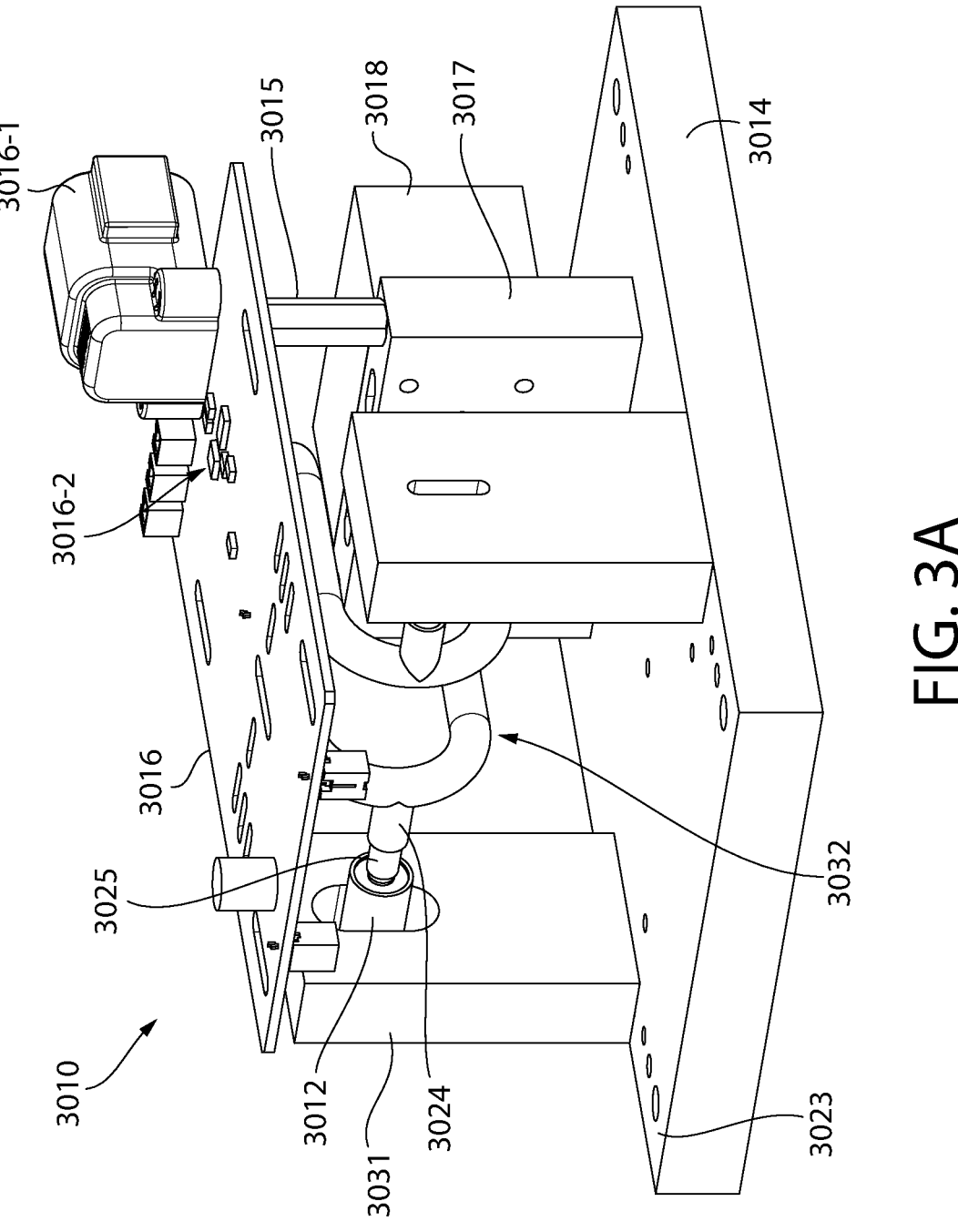
FIGS. 3A-3C are illustrations of an example slurry density meter or measurement device usable in the example analysis system, as described herein.
Figure 3B:
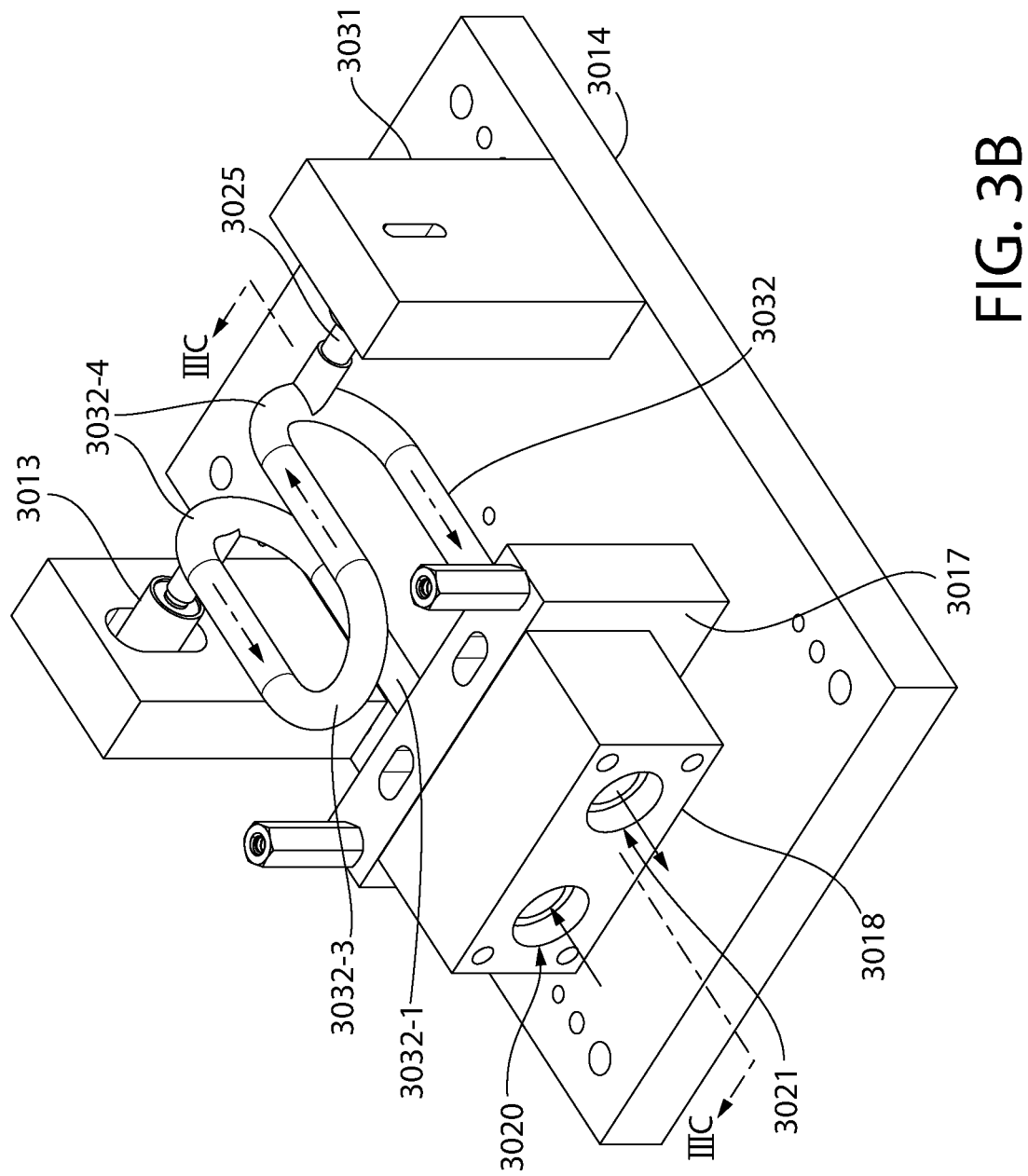
Figure 3C:
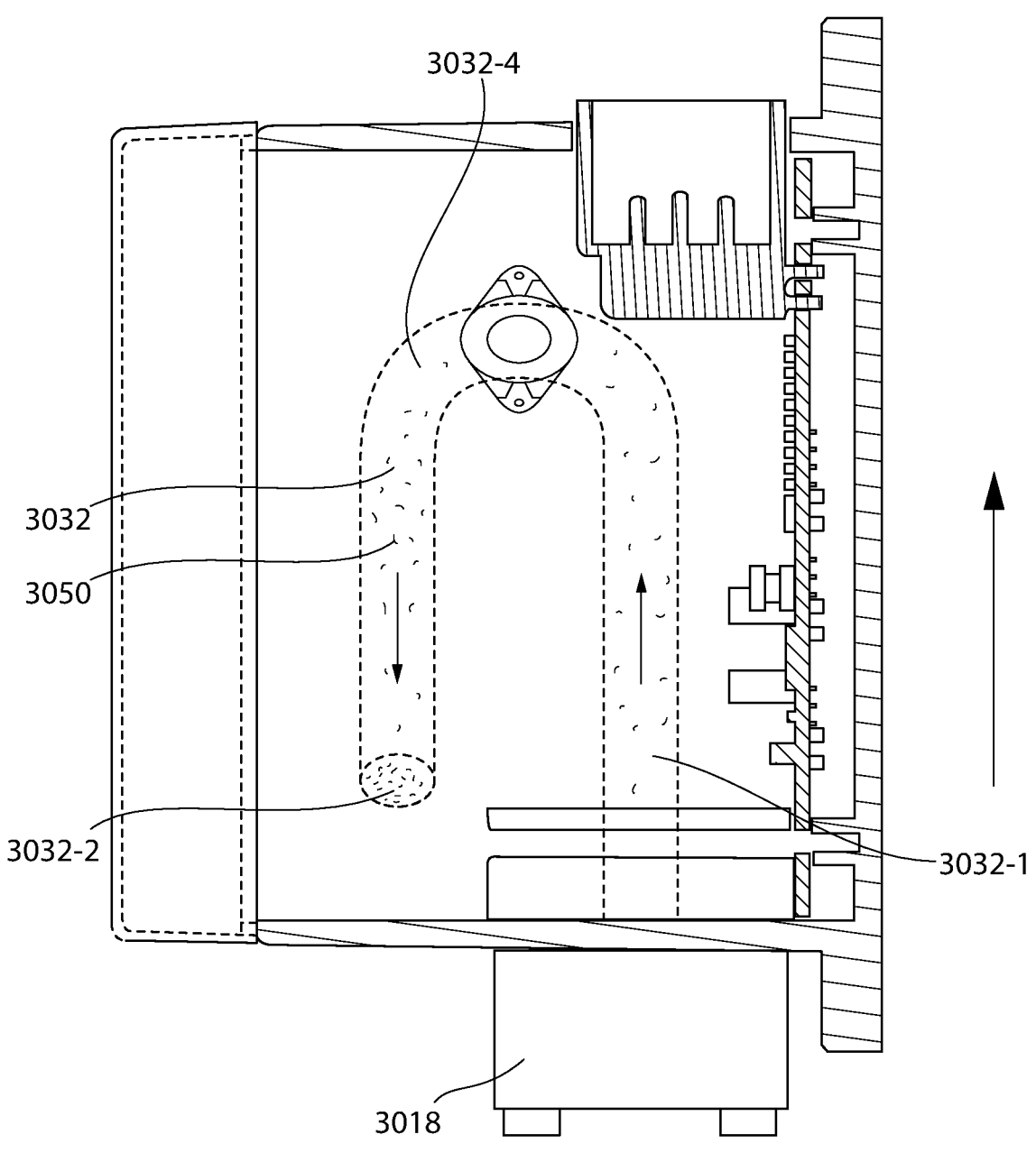

An example density measurement device 3010 is shown on FIGS. 3A-3C. Density measurement device 3010 may be the same as device 2020 (FIGS. 2A, 2B), although in examples density measurement device 3010 may be different than density measurement device 2020. As shown on FIGS. 3A-3C, density measurement device 3010 may include one or more components. For example, density measurement device 3010 may include an oscillator tube 3032, as described herein. Density measurement device 3010 may include a base 3014, a plurality of spacers 3015, a tube mounting block 3017, a flow connection manifold 3018, at least one or a pair of permanent magnets 3025, an electronic circuit control board 3016 and an electrical-communication interface unit 3016-1 configured for both electrical power supply for the board and communication interface to one or more system controllers.

Base 3014 may be configured for mounting the density measurement device 3010. For example, base 3014 may be configured for mounting the density measurement device 3010 on a flat horizontal support surface, vertical support surface, or support surface disposed at any angle therebetween. Accordingly, any suitable corresponding mounting orientation of the base may be used as desired. The mounting orientation of the base may be determined by the intended direction of oscillation of the oscillator tube 3032 taking into account the force of gravity on the slurry laden oscillator tube. In examples, as it may be advantageous to mount slurry passages in the oscillator tube in a manner that achieves the highest percent of horizontal passages as possible, base 3014 may be oriented in many and/or varied ways.

Oscillator tube 3032 may have one or more portions, such as one or more straight portions 3032-1 and/or one or more curved portions, such as lower curved portion 3032-3 or upper curved portion 3032-4. As shown on FIG. 3C, the mounting orientation of the base may be oriented such that the straight portions 3032-1 of tube 3032 are oriented in a vertical (or substantially vertical) direction and/or orientation. By orienting the straight portions of tube in a vertical direction and/or orientation, acceleration (e.g., acceleration due to gravity) may cause and/or allow particles (e.g., dense particles, large particles, non-homogenous particles) to settle. For example, by orienting the tube in a vertical direction and/or orientation, acceleration (e.g., acceleration due to gravity) may cause and/or allow particles (e.g., dense particles, large particles, non-homogenous particles) to settle when the slurry stops flowing (or slowly flows) through the density measurement device 3010 (e.g., u-tube 3032). The particles may settle in one or more portions of u-tube 3032, such as in one or more legs of u-tube 3032, at a bottom portion 3032-2 of u-tube 3032, in a curved portion (such as lower curved portion 3032-3), outside of u-tube 3032 (e.g., via the particles exiting u-tube 3032, such as via through holes of the flow connection manifold 3018), and the like. The particles may settle longitudinally from anti-node(s) to node(s), or vice-versa. The settled particles may not participate in the oscillation of the u-tube 3032, and therefore may not attribute to the density measurement. By determining the density measurement of the slurry including the particles (e.g., when the particles are not settled) and/or determining the density measurement of the slurry non including the particles (e.g., when the particles are settled), the density (e.g., total density) of the slurry may be determined and/or corrected, as described herein.

Values related to the settling of the particles may be determined, in examples. For example, the time at which the particles are fully settled, mostly settled, and the like, may be determined. The time it takes to achieve a steady state frequency from when the slurry is flowing until the slurry is stopped (e.g., stagnant) may be determined. The frequency change (e.g., absolute frequency change, percent frequency change, etc.) may be determined. For example, the absolute frequency change after a period of time (e.g., a predefined period of time) from when the slurry is flowing to when the slurry is stopped may be determined. The percent frequency change after a set time interval (e.g., set time interval from when the slurry is flowing to when the slurry is stopped) may be determined.

As described herein, flow of the material (e.g., slurry) through density measurement device 3010 may be adjusted. For example, flow of the material through density measurement device 3010 may be stopped, slowed, sped up, and the like. Flow of the material may be stopped, started, reduced, or sped up via a pump (e.g., pump 2081), stopped or started via a valve (e.g., valve 2008A), and the like. The density of the material may be determined when the material is flowing through density measurement device 3010, and/or the density of the material may be determined upon the flow being adjusted (e.g., stopped). For example, upon the flow being stopped, the density of the material may be determined. The density of the material may be determined upon a predetermined time (e.g., a predetermined time from the stoppage of the flowing material). By adjusting (e.g., stopping) the flow of the material, particles (e.g., relatively large particles) may fall (e.g., settle) to one or more portions of the u-tube 3032, such as the bottom 3032-2 of the vertically aligned oscillator tube 3032, one or more portions of legs of the density measurement device, outside of oscillator tube 3032, and the like. The particles (e.g., dense particles, large particles, non-homogenous particles) that settle may not be determined as part of the density measurement of the slurry. A correction factor of the density measurement of the slurry may be determined based on the particles that have settled. The correction factor may be applied to modify (e.g., correct) the density measurement of the slurry and/or the soil of the slurry.

As described herein, orienting the density measurement device 3010 (e.g., u-tube 3032) in a vertical (e.g., substantially vertical orientation) and/or stopping the flow of the slurry within the density measurement device 3010 (e.g., u-tube 3032) may improve accuracy of the determination of the density measurement (e.g., total density measurement) of the slurry. The improved accuracy of the total density measurement of the slurry may result in the improved determination of the soil to water mass ratio measurement of the slurry (e.g., soil slurry).

The u-tube may oscillate to determine the density of the slurry. The u-tube may oscillate when the slurry is flowing through density measurement device 3010 and/or the u-tube may oscillate when the slurry is not flowing through density measurement device 3010. The u-tube may oscillate to determine the density of the slurry when the slurry is flowing through the density measurement device 3010 and when the slurry is not flowing through the density measurement device 3010. For example, flow through the u-tube may be stopped (e.g., paused) within the density measurement device 3010 (e.g., u-tube 3032 of the density measurement device 3010) when pumping of the fluid is stopped (e.g., paused). When flow stops, the u-tube 3032 may continue to oscillate and particles 3050 (e.g., large particles, non-homogeneous particles, etc.) within the slurry may settle at one or more portions of the density measurement device 3011, such as at the bottom 3032-2 of the u-tube 3032 or legs of the density measurement device 3010, based on gravity. The density of the slurry during the stoppage (e.g., pause) in flow and the density of the slurry during the slurry flowing may be determined.

As the slurry flows through density measurement device 3010, the u-tube 3032 may oscillate. As the slurry is flowing, particles 3050 within the slurry may not settle at one or more portions of the density measurement device 3011. The density of the slurry during the flowing of the slurry may be determined. The density (e.g., total density) of the slurry during the stoppage (e.g., pausing) may be compared with the density (e.g., total density) of the slurry when flowing through the density measurement device 3010 (e.g., u-tube 3032). The density of the slurry during the stoppage (e.g., pausing) may be compared with the density of the slurry when flowing through the density measurement device 3010 (e.g., u-tube 3032) to improve the determination of the density (e.g., total density) of the slurry. For example, the difference in density measurement (e.g., during oscillation of u-tube 3032) in a non-settled and at least partially settled state allows for correction of the density measurement in the normally flowing state. The density of the slurry during the stoppage (e.g., pausing) may be compared with the density of the slurry when flowing through the density measurement device 3010 (e.g., u-tube 3032) because large, suspended particles may not contribute to (e.g., are not substantially affected by) the oscillation provided the u-tube 3032.

The oscillation frequency of the density measurement device 3010 may be related (e.g., directly related) to a mass (e.g., a mass of the fixed volume of fluid within the oscillating portion of the density measurement device 3010) and the centroid of fluid mass in relation to the node(s) and anti-node(s) of vibration. Large particles suspended in the fluid may not participate (e.g., fully participate) in the oscillation of tube 3032. By not participating in the oscillation of the tube 3032, an error in the density measurement may be provided by the density measurement device 3010. By measuring the oscillation frequency when fluid is flowing through the density measurement device 3010, it may be possible to determine the mass (e.g., a mass of the fixed volume of fluid within the oscillating portion of the density measurement device 3010) and the centroid of fluid mass in relation to the node(s) and anti-node(s) of vibration. The mass of the particles when the when fluid is flowing through the density measurement device 3010 may include all particles (e.g., big particles, small particles, etc.).

By measuring the oscillation frequency when fluid is not flowing through the density measurement device 3010, it may be possible to determine the mass (e.g., a mass of the fixed volume of fluid within the oscillating portion of the density measurement device 3010) and the centroid of fluid mass in relation to the node(s) and anti-node(s) of vibration. The mass of the particles when the fluid is not flowing through the density measurement device 3010 may include small (e.g., relatively small) particles, as the large particles may settle to one or more portions of the density measurement device 3010 (e.g., the bottom of the vertical oscillation tube 3032 and/or one or more of the legs of the density measurement device 3010). Accordingly, determining the density measurement of the slurry when the fluid is not flowing through the density measurement device may allow for correction of the determination of the density measurement of the slurry when the fluid is flowing. Such correction may result in a more accurate determination of the density (e.g., total density) of the slurry.

As the oscillation frequency is related to the mass of the fixed volume of fluid within the oscillating portion of the device and the centroid of fluid mass in relation to the node(s) and anti-node(s) of vibration, an indication of the mass may be determined via one or more of the following. For example, the oscillation frequency change (e.g., absolute oscillation frequency) may be determined after a predetermined period of time. In another example, the percentage of oscillation frequency change may be determined after a predetermined period of time. In another example, the time to a steady state or defined minimum rate of frequency change may be determined.

The oscillation frequency (e.g., absolute, percentage) of a homogeneous material (e.g., clay) may not change over time when flow is stopped, and the oscillation frequency of a non-homogeneous material (e.g., sand) may change over time when flow is stopped. A homogeneous material (e.g., clay) may not drop out of suspension (e.g., may not drop out of the tube 3032). A non-homogeneous material (e.g., sand) may drop out of suspension (e.g., may drop out of the tube 3032). As a homogeneous material (e.g., clay) may not drop out of suspension, the oscillation frequency of the homogeneous material may not change (e.g., substantially change). As the oscillation frequency of the homogeneous material may not change (e.g., substantially change), the mass of the homogeneous material may not change (e.g., may not change as it flows through tube 3032). Because the mass of the homogeneous material may not change, the density measurement of a slurry containing the homogeneous material may be consistent (e.g., accurate).

As a non-homogeneous material (e.g., sand) may drop out of suspension, the oscillation frequency of the non-homogeneous material may change (e.g., substantially change). As the oscillation frequency of the non-homogeneous material may change (e.g., substantially change), the mass of the non-homogeneous material may change. Because the mass of the non-homogeneous material may change, the density measurement of a slurry containing the non-homogeneous material may be inconsistent (e.g., inaccurate). By taking a measurement of the fluid (e.g., flowing fluid) to achieve a base density measurement, then stopping flow and measuring the density (e.g., measuring the density again) after a predetermined time interval, a relative amount of large particles can be determined, and a corresponding correction factor or offset can be applied to the density measurement.

Base 3014 may substantially planar and rectangular in an example, although other polygonal and non-polygonal shaped bases may be used. The base 3014 may include a plurality of mounting holes 3023 to facilitate mounting the base to the support surface with a variety of fasteners. Base 3014 may define a longitudinal centerline of the density measurement device 3010 which may be aligned with the length of the oscillator tube 3032 (parallel to the tube's parallel legs). For example, the length of the oscillator tube 3032 may extend along the centerline. In an example, centerline and the flow passages within oscillator tube 3032 may be horizontal so that any settling that occurs may be perpendicular to the flow through the passage rather than in-line with the flow. In other examples, as described herein, at least a majority of the flow passages inside the oscillator tube may oriented vertically, substantially vertically, or the like.

Spacers 3015 may be elongated in structure and space the control board 3016 apart from the base 3014 so that the oscillator tube 3032 may occupy the space 3015-1 created therebetween. Any suitable number of spacers may be used for this purpose. The space may be sized to provide clearance for accommodating the motion of the oscillator tube 3032 and other appurtenances such as the frequency driver and pickup 3012, 3013. The planar control board 3016 may be oriented parallel to the base 3014.

As described herein, the density measurement device 3010 may include a u-shaped oscillator tube 3032. The U-shaped oscillator tube 3032 may be excited via a frequency transmitter or driver 3012 to oscillate the tube at its characteristic natural frequency. In examples, the driver 3012 may be an electromagnetic inductor, a piezoelectric actuator/element, a mechanical pulse generator, and the like. The driver 3012 may be operable to generate a user-controllable and preprogrammed excitation frequency. A corresponding sensor such as a receiver or pickup 3013 may be provided.

Density measurement device 3010 may include a standoff, such as standoff 3024. Standoff 3024 may be a non-magnetic standoff. The standoff 3024 may project transversely outwards from the lateral sides of oscillator tube in opposite directions and perpendicular to the longitudinal centerline of the density measurement device 3010. Standoff 3024 may be configured with dimensions and/or lengths to space magnets far enough away from the oscillator tube 3032 to prevent creating a static magnetic field of sufficient strength within tube 3032 to attract and/or aggregate particles (e.g., iron particles) in the soil slurry.

Pickup 3013 may be configured to detect and obtain a vibrational measurement of the oscillator tube when excited. Pickup 3013 may be electromagnetic, inductance, piezoelectric receiver/element, optical, or other commercially available sensor capable of detecting and measuring the vibrational frequency response of the oscillator tube 3032 when excited. The pulsing or vibrational response movement of the excited oscillator tube 3032 may be detected by pickup 3013, which may measure the amplitude of the frequency response of the tube. The amplitude of the frequency response of the tube may be highest at a natural/resonance or secondary harmonic frequency when the tube is empty. In another example, the phase difference between the driving and driven frequencies may be used to narrow into the natural frequency.

When excited, the vibrational frequency of oscillator tube 3032 may change relative to the density of the slurry (e.g., when stagnantly filled in the oscillator tube for batch mode density measurement or flowing through the U-tube at a continuous and constant flow rate for continuous density measurement). The density measurement device may convert the measured oscillation frequency into a density measurement (e.g., via a digital controller) which may be programmed to compare the baseline natural frequency of the empty tube and/or the baseline frequency of the tube filled with a fluid of known density (e.g. water) to the slurry filled tube. For example, two or more points may be created by measuring the frequency when the tube 3032 is empty and measuring with water. The calibration may be used to determine the density of one or more particles (e.g., any particles) that may flow through tube 3032.

The frequency driver and pickup 3013 may be operably and communicably coupled to an electronic control circuit comprising a microprocessor-based density meter processor or controller 3016-2 mounted to a circuit control board 3016 supported from base 3014. Controller 3016-2 may be configured to deliver a pulsed excitation frequency to the oscillator tube 3032 via the driver 3012, and measure the resultant change in the resonant frequency and phase of the excited oscillator tube. The digital density measurement device 2022 may convert the measured oscillation frequency into a density measurement via the controller which is preprogrammed and configured with operating software or instructions to perform the measurement and density determination. The controller 3016-2 may be provided and configured with all of the usual ancillary devices and appurtenances similar to any of the controllers already previously described herein and necessary to provide a fully functional programmable electronic controller. Accordingly, these details of the density meter controller 3016-2 will not be described in further detail for the sake of brevity.

The frequency driver 3012 and pickup 3013 may be mounted (e.g., rigidly mounted) to circuit board 3016 in an example. In other examples, the driver and pickup may be rigidly mounted to separate vertical supports 3031 attached to base 3014. The driver and pickup may be mounted adjacent and proximate to permanent magnets 3025. Magnets (e.g., permanent magnets) 3025 may generate a static magnetic field (lines of magnetic flux) which may interact with the driver 3012 and/or pickup 3013 for exciting the oscillator tube 3011 and measuring its vibrational frequency when excited.

Tube mounting block 3017 may be configured for mounting (e.g., rigidly mounting) oscillator tube 3032 in a cantilevered manner. Oscillator tube 3032 may be a straight U-tube configuration in which all portions lie in the same plane (e.g., vertical plane, horizontal plane). The mounting block 3017 may include one or more (e.g., a pair) of through bores which may receive the end portions of the oscillator tube 3032 (e.g., completely therethrough). A portion of the oscillator tube 3032 may be unsupported and able to freely oscillate in response to the excitation frequency delivered by the driver 3012.

An inlet end portion and outlet end portion of oscillator tube 3032 may project through and beyond the tube mounting block 3017. The inlet end portion and outlet end portion of oscillator tube may be received in a corresponding open through bore or hole of the flow connection manifold 3018 associated with defining a slurry inlet 3020 and slurry outlet 3021 of the connection manifold 3018. Through holes 3018 of the flow connection manifold 3018 may have any suitable configuration to hold the end portions of oscillator tube 3032 in tight and a fluidly sealed manner. Suitable fluid seals such as O-rings, elastomeric sealants, or similar may be used to achieve a leak-tight coupling between the oscillator tube and connection manifold 3018. The connection manifold 3018 may abuttingly engage the mounting block 3017 to provide contiguous coupling openings therethrough for the inlet end portion and/or outlet end portion to fully support the end portions of oscillator tube 3032. In examples, the connection manifold 3018 may be spaced apart, in relative close proximity to mounting block 3017, or one or more other configurations.

The mounting block 3017, flow connection manifold 3018, and base 3014 may be made of a suitable metal (e.g. aluminum, steel, etc.) of sufficient weight and thickness to act as vibration dampeners such that excitation of oscillator tube which is measured by the density measurement device 3010 is indicative of only the frequency response of the filled oscillator tube 3011 without interference by any corresponding parasitic resonances that otherwise could be induced in the base or the mounting block and flow connection manifold.

Oscillator tube 3032 may have a conventional U-shape, as shown, although other shapes may be used. Oscillator tube 3032 may be formed of a non-metallic material in an example. Suitable materials may include glass, such as borosilicate glass. In other examples, metallic tubes may be used such as without limitation stainless steel which is less fragile and non-magnetic. Magnets 3025 may be fixedly and rigidly supported from and mounted to the oscillator tube 3032, such as on opposite lateral sides of the U-tube proximate to the U-bend portion. The U-bend portion may be farthest from the cantilevered portion of the oscillator tube adjoining the mounting block 3017 and may experience the greatest displacement/deflection when excited by driver 3012 making the tube vibration frequency change readily detectible by the digital meter controller 3016-2. Making the tube vibration frequency change readily detectible may create an improved sensitivity for frequency deviation measurement of the slurry-filled oscillator tube 3011 versus the natural frequency of the tube when empty; the deviation or different in frequency being used by controller 3016-2 to measure the slurry density.

As described herein, it may be necessary to know (e.g., determine) the water to soil ratio (e.g., ratio of carrier fluid mass to solid particle mass) to perform analysis of a slurry. For example, it may be necessary to know the ratio of carrier fluid mass to solid particle mass to ensure that appropriate extractant quantities are used and/or that downstream analyte concentration calculations are performed (e.g., performed properly). The determination of the water to soil ratio may be based on one or more of a particle density measurement of one or more solids within the slurry, a density measurement of the slurry (e.g., the entire slurry), a density of the fluid within the slurry, and the like.

Figure 4:
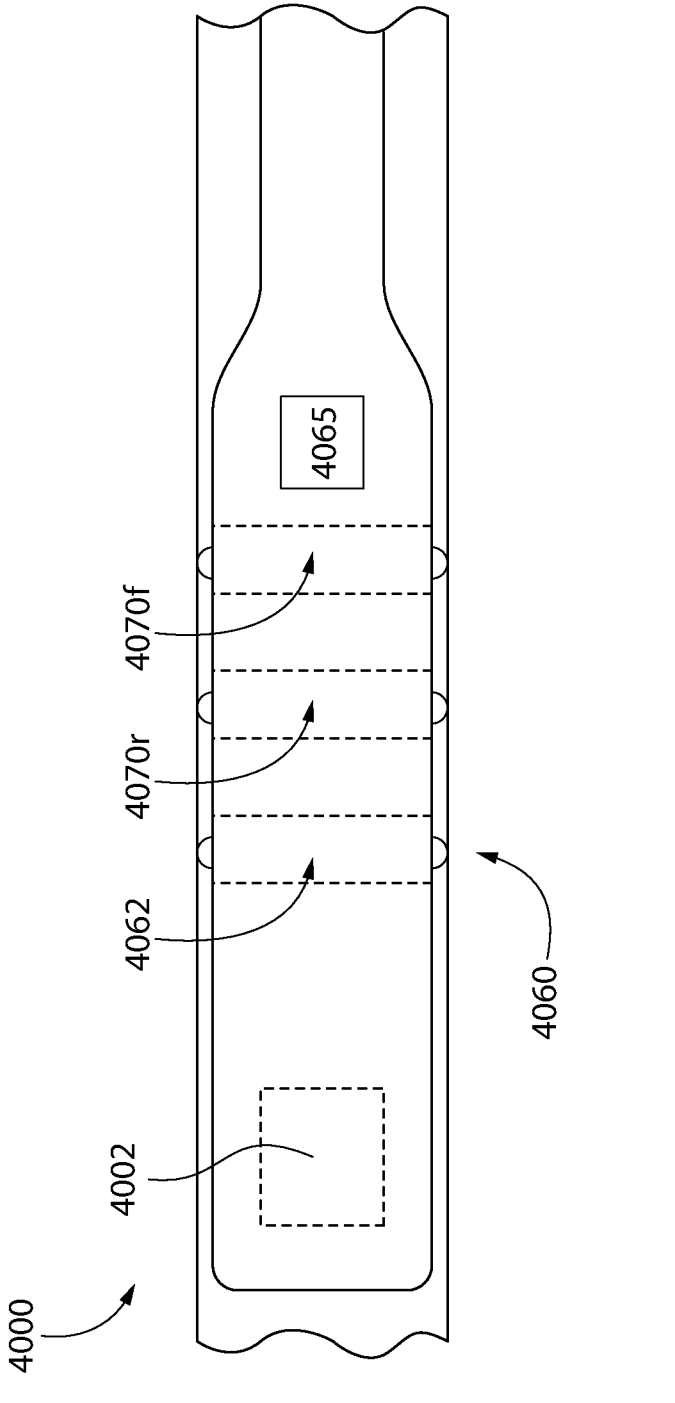
FIG. 4 is an illustration of an example particle density measurement device usable in the example analysis system, as described herein.

FIG. 4 shows an example particle density measurement device 4000. Particle density measurement device 4000 may be device 2022, as shown on FIGS. 2A, 2B. Particle density measurement device 4000 may be described as a soil particle density measurement device 4000 throughout the disclosure, although it should be understood that this is for illustration purposes only and the particle density measurement device 4000 may determine the value of one or more attributes of one or more agricultural solids in a slurry. The one or more values of the one or more attributes determined by particle density measurement device 4000 may be in addition, or in the alternative, of the particle density measurement device 4000 determining the particle density measurement of a solid within a slurry. For example, the particle density measurement device 4000 (or one or more other devices, such as devices similar to particle density measurement device 4000) may determine the mass of one or more solids in a slurry, the electrical conductivity of one or more solids in a slurry, and the like. In an example, particle density device 4000 (or one or more devices similar to particle density measurement device 4000) may be used to determine the mass of organic matter within a slurry. In examples one or more devices separate from particle density device 4000 may be used to determine the mass of organic matter within a slurry.

Particle density measurement device 4000 (or one or more devices similar to particle density measurement device 4000) may determine and/or detect characteristics of a sample (e.g., a soil sample, such as a soil sample from a soil slurry). Such characteristics of the sample may include soil moisture, soil organic matter, soil temperature, seed presence, seed spacing, percentage of seeds firmed, soil residue presence, as described herein. Soil particle density measurement device 4000 may generate soil signals via one or more sensing techniques relating to soil and/or slurry samples. For example, soil particle density measurement device 4000 may generate soil signals via one or more of optical wavelength reflectance/absorption values, electromagnetic wavelength reflectance/absorption values, temperature values, electrical current flow values, electrical conductivity, Xray fluorescence, Laser-Induced Breakdown Spectroscopy, Near Infrared Spectroscopy, Mid Infrared Spectroscopy, Far Infrared Spectroscopy, Xray Diffraction, Gamma Ray emission, Raman Spectroscopy, Multi-Spectral Sensing, Short wave infrared, Microfluidics, Acoustic resonance spectroscopy, Fourier Transform Infrared Spectroscopy, Photoemission spectroscopy, spectrophotometry, thermal infrared spectroscopy, video spectroscopy, hyperspectral imaging, laser diffraction, and the like.

Particle density measurement device 4000 may include one or more reflectivity sensors 4002. Each reflectivity sensor 4002 may be disposed and/or configured to measure reflectivity of soil. For example, the reflectivity sensors 4002 may be disposed to measure soil (e.g., soil sample). The reflectivity sensor 4002 may include a lens disposed in the bottom of the body of the soil particle density measurement device. In examples the reflectivity sensor 4002 may include one of the examples disclosed in WO2014/153157, WO2014/186810, WO2015/171908, US20180168094, WO2019070617, and/or WO2020161566. In one embodiment, reflectivity sensor 4002 may be a SmartFirmer® sensor available from Precision Planting LLC of Tremont, Illinois. In examples, the reflectivity sensor 4002 may be configured to measure reflectivity in the visible range (e.g., 400 and/or 600 nanometers), in the near-infrared range (e.g., 940 nanometers) and/or elsewhere the infrared range. One or more mechanisms may be provided for cleaning of one or more components of particle density measurement device 4000. For example, one or more ports (e.g., fluid ports) may be provided for cleaning one or more sensors of particle density measurement device 4000. The one or more ports may provide one or more substances, such as water and/or air, to clean one or more of the sensors.

The soil particle density measurement device 4000 may include a temperature sensor 4060. The temperature sensor 4060 may be disposed and/or configured to measure temperature of soil. Central portion 4062 of soil particle density measurement device 4000 may include a thermally conductive material, such as copper. The central portion 4062 may include a hollow copper rod. The central portion 4062 may be in thermal communication with a thermocouple fixed to the central portion. In other examples, the temperature sensor 4060 may include a non-contact temperature sensor such as an infrared thermometer.

As described herein, particle density measurement device 4000 may determine the density of one or more solids (e.g., soil) within a slurry. In addition, or alternatively, particle density measurement device 4000 may determine values of the materials of the solid (e.g., soil) within the slurry. For example, the particle density measurement device 4000 (or a device similar to particle density measurement device 4000) may determine values of organic matter and/or minerals within a slurry. As an example, the particle density measurement device 4000 may determine the mass (e.g., relative mass) of the organic matter and/or minerals within the slurry. As known by those of skill in the art, organic matter is a property that may affect soil productivity. The particle density measurement device 4000 may determine organic matter within the slurry by measuring reflectance of the slurry (e.g., soil slurry) as the slurry flows past the particle density measurement device 4000. The particle density measurement device 4000 may measure reflectance via a sensor (such as sensor 4002) using multiple wavelengths in the visible and/or infrared spectrums, for example. The sensor may use sensing techniques including optical wavelength reflectance/absorption values, electromagnetic wavelength reflectance/absorption values, temperature, electrical current flow, electrical conductivity, Xray fluorescence, Laser-Induced Breakdown Spectroscopy, Near Infrared Spectroscopy, Mid Infrared Spectroscopy, Far Infrared Spectroscopy, Xray Diffraction, Gamma Ray emission, Raman Spectroscopy, Multi-Spectral Sensing, Short wave infrared, Microfluidics, Acoustic resonance spectroscopy, Fourier Transform Infrared Spectroscopy, Photoemission spectroscopy, spectrophotometry, thermal infrared spectroscopy, video spectroscopy, hyperspectral imaging, laser diffraction, and the like.

The soil particle density measurement device 4000 may include a plurality of electrical conductivity sensors 4070r. Electrical conductivity sensor 4070r may be disposed and/or configured to measure electrical conductivity of soil. In examples, the electrical conductivity sensors 4070r may include one or more ground-working or ground-contacting devices (e.g., discs or shanks) that contact the soil and are electrically isolated from one another or from another voltage reference. The voltage potential between the sensors 4070r or other voltage reference may be measured by the soil particle density measurement device 4000. The voltage potential or another electrical conductivity value derived from the voltage potential may be reported to a user of soil particle density measurement device 4000. The electrical conductivity value may be associated with a GPS-reported position (e.g., position relating to the sample) and/or used to generate a map of the spatial variation in electrical conductivity throughout the field. It should be appreciated that at least one of the electrical conductivity sensors may be electrically isolated from one or more other sensors or voltage references.

The soil particle density measurement device 4000 may include a plurality of electrodes 4070f. The plurality of electrodes 4070f may be operably coupled to, or integrated/contained with the one or more electrical conductivity sensors 4070r. Sensors 4070r are operably coupled in turn to system controller 6820 in one embodiment to communicated electrical conductivity measurements therebetween. The plurality of electrodes 4070f associated with electrical conductivity sensors 4070r may use one or more sensing techniques to determine the conductivity of the slurry (e.g., the soil within the slurry) via direct immersion into the slurry. For example, the plurality of electrodes 4070f and/or the electrical conductivity sensors 4070r may use one or more sensing techniques including electrical current flow, electrical conductivity, electro-magnetic induction, electrical resistivity, time domain reflectometry, amplitude domain reflectometry, frequency domain reflectometry, and the like.

One or more of the electrodes 4070f associated with electrical conductivity sensors 4070r may be spaced so that they span across and/or at least partially surround the flow of the slurry (e.g., soil slurry) to measure the density of the agricultural solids within the slurry. For example, an electrode may be placed on one side of the flow of the slurry, and another electrode may be placed on another opposite side of the flow of the slurry (i.e. the slurry stream). Electrodes 4070f are in direct wetted contact with the flowing slurry. Electrodes 4070f may measure electrical conductivity in contact with one or more sides (e.g., either side) of the soil slurry. For example, as slurry flows through a tube such as flow conduit 2059, electrodes 4070f may measure electrical conductivity in contact with one or more sides (e.g., either side) of the soil slurry flowing through the tube. Electrical conductivity of the slurry (e.g., electrical conductivity of the soil within the slurry) may be determined via electrodes 4070f. The electrical conductivity of the slurry (e.g., electrical conductivity of the soil within the slurry) may be used to determine the amount(s) of nutrients in the slurry, for example, for plant uptake and/or soil salinity. In another example, the electrical conductivity of the slurry (e.g., electrical conductivity of the soil within the slurry) may be used to determine the particle density measurement of the slurry (e.g., the soil density within the slurry).

Data from the particle density measurement device 4000 may be transmitted and/or received via communications interface 4065. The particle density measurement device 4000 may transmit the data for processing of the data, storage of the data, displaying the data, and the like. For example, data from the particle density measurement device 4000 may be transmitted to a mobile device (e.g., a smart phone or tablet), an external server (e.g., a cloud server), one or more Internet of Things devices, and the like, for processing, storage, and/or display. In examples communications interface 4065 may be a wireless transmitter, although communication may be performed via one or more known methods in other examples.

Figure 5A:
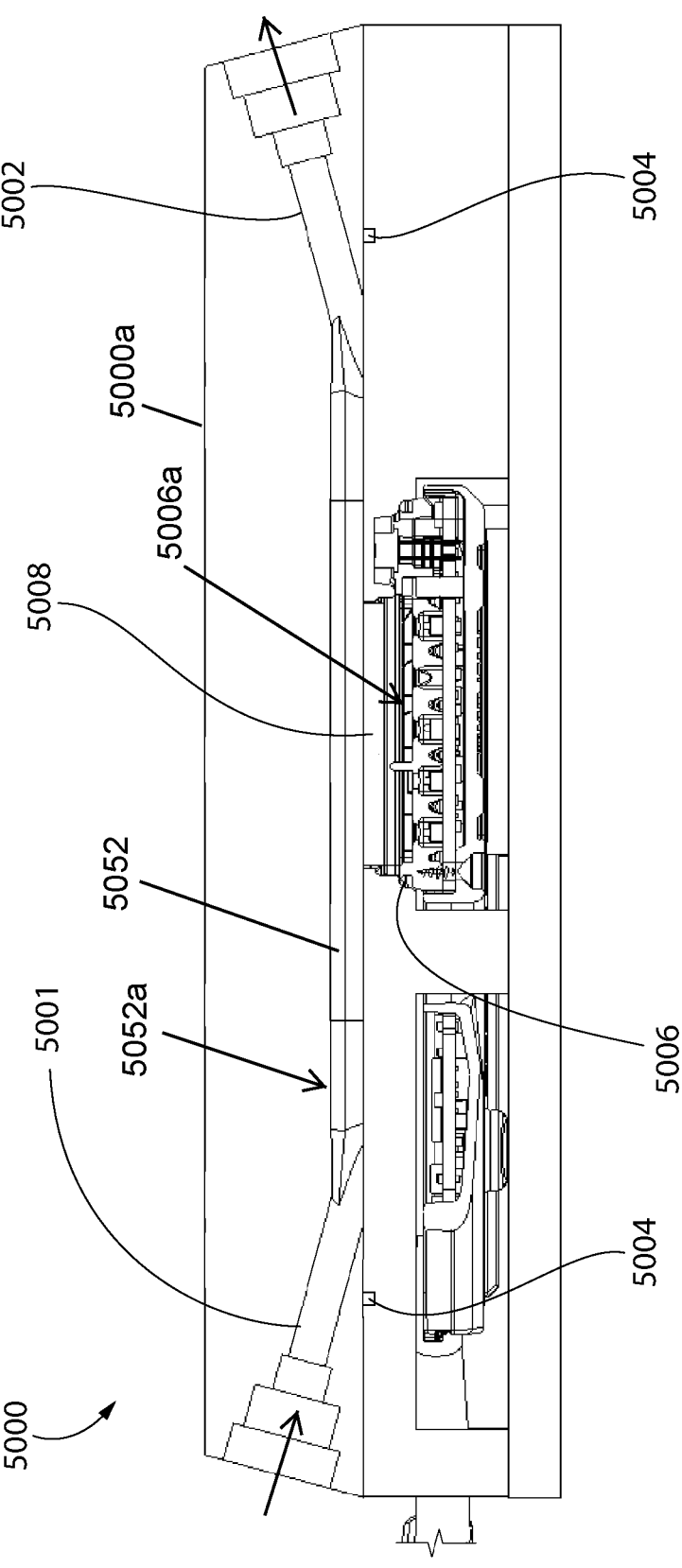
FIGS. 5A and 5B are longitudinal and transverse cross sectional views of a reflectance type particle density measurement device usable in the example analysis system, as described herein.
Figure 5B:
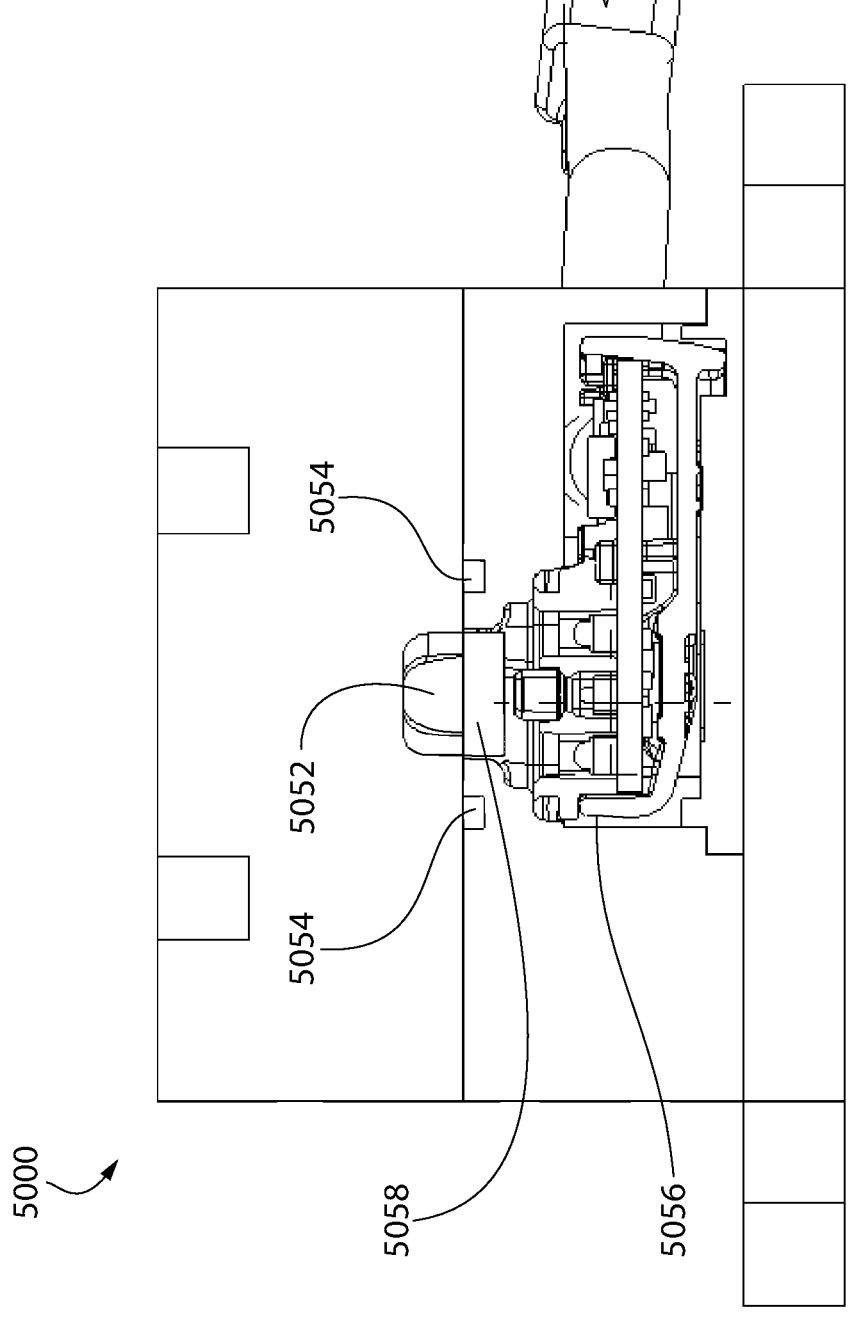

Additional examples of a reflectance type particle density measurement device are shown as device 5000 in FIGS. 5A and 5B for measuring characteristics of an agricultural material solid such as soil or other contained in aqueous slurry. The particle density measurement device 5000 (e.g., one or more optical sensors) may measure reflectance of the soil solids in the slurry dynamically while the slurry is in a flowing state through the device. For example, the particle density measurement device 5000, 5050 (e.g., sensor(s)) may measure reflectance of the soil slurry flowing past the particle density measurement device 5000, 5050 (e.g., sensor) using one or more (e.g., multiple) wavelengths in the visible and infrared spectrums.

Soil particle density measurement device 5000 comprises an elongated housing 5000a which includes one or more slurry inlets 5001 and slurry outlets 5002. In the illustrated embodiment, a single inlet and outlet are provided. Inlets and/or outlets 5001, 5002 may be configured to receive slurry and discharge or release slurry from soil particle density measurement device 5000. In examples the inlet 5001 may (e.g., may only) receive fluids such as an agricultural material slurry (e.g., soil slurry) and the outlet 5002 may (e.g., may only) discharge or release fluids such as the slurry. In other examples, each of the inlet and outlet may receive and release fluids. Soil particle density measurement device 5000 may include one or more O-rings 5004, for example, to seal an upper part of housing 5000a caps to a lower base part of soil particle density measurement device 5000 as shown. Soil particle density measurement device 5000 may include one or more optics devices, printed circuit boards (PCBs), lenses, and the like. The optical sensor may be mounted to the PCB. For example, soil particle density measurement device 5000 may include one or more optics and/or PCBs 5006.

Soil particle density measurement device 5000 may include one or more lenses, such as one or more sapphire lenses 5008 located adjacent to flow channel 5052a which extends linearly between slurry inlet and outlet 5001, 5002 as shown. Flow channel 5052 conveys the agricultural slurry through the reflectance particle density measurement device thereby defining a flow path 5052 therethrough for conducting reflectance measurements via the sensor 5006a. The sensor is disposed adjacent to the flow channel to measure the reflectance of the solid in the slurry as the slurry flows through the flow path. The sapphire lens 5008 provides a liquid sealed view into the flow channel 5052a through which the sensor 5006a measures the reflectance of the solid within the slurry as the slurry flows along the flow path through measurement device 5000. It bears noting that other configurations of particle density measurement device may be used.

FIG. 6 shows an example controller for controlling the systems and apparatuses described herein. For example, the example controller may control operation of one or more systems and sub-systems, such as collection sub-system 1001, preparation sub-system 1002, analysis sub-system 1003. The example controller may control operation of system 2000. The control and/or operations described within this disclosure may be performed by one or more processors, as described herein. For example, the operations described herein may be controlled and/or monitored (e.g., automatically controlled and monitored) by a processor-based control system 6800 including a programmable central processing unit (CPU) (e.g. processing system), such as system controller 6820. System controller 6820 is disclosed in co-pending U.S. Patent Application Publication No. 2018/0124992A1, PCT Publication No. WO2020/012369, PCT Application No. PCT/IB2021/051077, filed on 10 Feb. 2021, and/or PCT Application No. PCT/IB2021/052872, filed on 7 Apr. 2021. As further described herein, system controller 6820 may include one or more processors, non-transitory tangible computer readable medium, programmable input/output peripherals, and all other necessary electronic appurtenances normally associated with a fully functional processor-based controller.

FIG. 6 shows the control or processing system 6800 including programmable processor-based central processing unit (CPU) or system controller 6820 as referenced to herein. System controller 6820 may include one or more processors, non-transitory tangible computer readable medium, programmable input/output peripherals, and all other necessary electronic appurtenances normally associated with a fully functional processor-based controller. Control system 6800, including controller 6820, may be operably and communicably linked to one or more soil sample processing and analysis systems and devices described herein via suitable communication links 6752 to control operation of those systems and device in a fully integrated and sequenced manner.

In an example, the control system 6800 including programmable controller 6820 may be mounted on a translatable self-propelled or pulled machine (e.g., vehicle, tractor, combine harvester, etc.) which may include an agricultural implement (e.g., planter, cultivator, plough, sprayer, spreader, irrigation implement, etc.). In an example, the machine upon which the control system 6800 is attached may perform operations of a tractor or vehicle that is coupled to an implement for agricultural operations. In other examples, the controller may be part of a stationary station or facility. Control system 6800, whether onboard or off-board machine, may include the controller 6820, non-transitory tangible computer or machine accessible and readable medium such as memory 6805, and a network interface 6815.

Computer or machine accessible and readable medium may include any suitable volatile memory and non-volatile memory or devices operably and communicably coupled to the processor(s). Any suitable combination and types of volatile or non-volatile memory may be used including as examples, without limitation, random access memory (RAM) and various types thereof, read-only memory (ROM) and various types thereof, hard disks, solid-state drives, flash memory, or other memory and devices which may be written to and/or read by the processor operably connected to the medium. Both the volatile memory and the non-volatile memory may be used for storing the program instructions or software. In one example, the computer or machine accessible and readable non-transitory medium (e.g., memory 6805) may contains executable computer program instructions which when executed by the system controller 6820 cause the system to perform operations or methods of the present disclosure including measuring properties and testing of soil and vegetative samples.

While the machine accessible and readable non-transitory medium (e.g., memory 6805) is shown to be a single medium, the term should be taken to include a single medium or multiple media (e.g., a centralized or distributed database, and/or associated caches and servers) that store the one or more sets of control logic or instructions. The term "machine accessible and readable non-transitory medium" may be taken to include any medium that is capable of storing, encoding or carrying a set of instructions for execution by the machine and that cause the machine to perform any one or more of the methodologies of the present disclosure. The term "machine accessible and readable non-transitory medium" may be taken to include, but not be limited to, solid-state memories, optical and magnetic media, and carrier wave signals.

Network interface 6815 may communicate with the soil sample processing and analysis systems and devices described herein (collectively designated 6803 in FIG. 6), and other systems or devices. The network interface 6815 may be configured for wired and/or wireless bidirectional communications which may include at least one of a GPS transceiver, a WLAN transceiver (e.g., Wi-Fi), an infrared transceiver, a Bluetooth transceiver, Ethernet, Near Field Communications, or other suitable communication interfaces and protocols for communications with the other devices and systems. The network interface 6815 may be integrated with the control system 6800 as illustrated in FIG. 6, or elsewhere. The I/O (input/output) ports 6829 of control system 6800 (e.g., diagnostic/on board diagnostic (OBD) port) may enable communication with another data processing system or device (e.g., display devices, sensors, etc.).

The programmable controller 6820 may include one or more microprocessors, processors, a system on a chip (integrated circuit), one or more microcontrollers, or combinations thereof. The processing system may include processing logic 6826 for executing software instructions of one or more programs and a communication module or unit 6828 (e.g., transmitter, transceiver) for transmitting and receiving communications. The communication unit 6828 may be integrated with control system 6800 (e.g. controller 6820) or separate from the processing system. In an example, communication unit 6828 may be in operable data communication with one or more devices, systems, and/or sub-systems via a diagnostic/OBD port of the I/O ports 6829.

Programmable processing logic 6826 of the control system 6800 may direct the operation of system controller 6820 (e.g., including one or more processors) to process the communications received from the communication unit 6828 or network interface 6815 including agricultural data (e.g., test data, testing results, GPS data, liquid application data, flow rates, etc.), and soil sample processing and analysis systems and devices 6803 data. The memory 6805 of control system 6800 is configured for preprogrammed variable or setpoint/baseline values, storing collected data, and computer instructions or programs for execution (e.g. software 6806) used to control operation of the controller 6820. The memory 6805 can store, for example, software components such as testing software for analysis of soil and vegetation samples for performing operations of the present disclosure, or any other software application or module, images 6808 (e.g., captured images of crops), alerts, maps, etc. The system 6800 can also include an audio input/output subsystem (not shown) which may include a microphone and a speaker for, for example, receiving and sending voice commands or for user authentication or authorization (e.g., biometrics).

The system controller 6820 may communicate bi-directionally with memory 6805 via communication link 6830, network interface 6815 via communication link 6832, display devices 6830 and optionally a second display device 6825 via communication links 6834, 6835, and I/O ports 6829 via communication links 6836. System controller 6820 further communicates with the soil sample processing and analysis systems and devices 6803 via one or more wired/wireless communication links.

Display devices 6825 and 6830 may provide visual user interfaces for a user or operator. The display devices may include display controllers. In an example, the display device 6825 may be a portable tablet device or computing device with a touchscreen that displays data (e.g., test results of soil, test results of vegetation, liquid application data, captured images, localized view map layer, high definition field maps of as-applied liquid application data, as-planted or as-harvested data or other agricultural variables or parameters, yield maps, alerts, etc.) and data generated by an agricultural data analysis software application and receives input from the user or operator for an exploded view of a region of a field, monitoring and controlling field operations. The operations may include configuration of the machine or implement, reporting of data, control of the machine or implement including sensors and controllers, and storage of the data generated. The display device 6830 may be a display (e.g., display provided by an original equipment manufacturer (OEM)) that displays images and data for a localized view map layer, as-applied liquid application data, as-planted or as-harvested data, yield data, controlling a machine (e.g., planter, tractor, combine, sprayer, etc.), steering the machine, and monitoring the machine or an implement (e.g., planter, combine, sprayer, etc.) that is connected to the machine with sensors and controllers located on the machine or implement.

Figure 7:
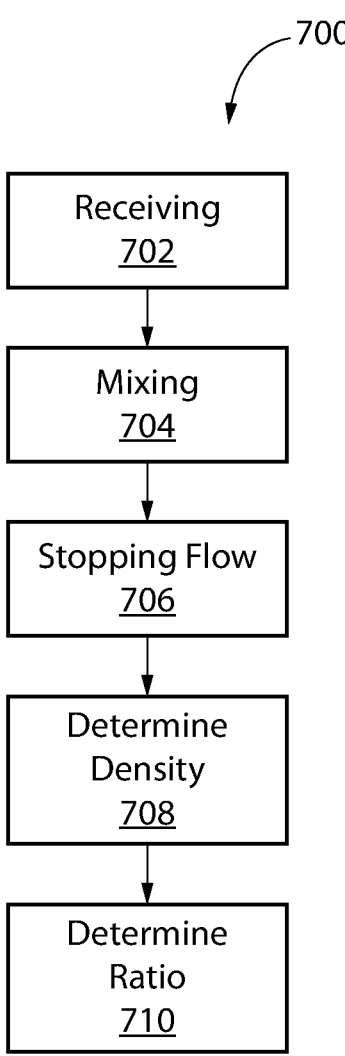
FIG. 7 is an example process of determining a ratio of a fluid and solid within a slurry, as described herein.

FIG. 7 shows an example process 700 for analyzing one or more agricultural materials. The agricultural materials may be one or more of, soil, manure, vegetation, water, or a combination of the soil, manure, vegetation, water (e.g., a slurry). At 702, agricultural materials including a solid and a liquid may be received, for example, via one or more inlets. At 704, the one or more agricultural materials may be mix via a mixing device. At 706, the flow of the one or more agricultural materials may be stopped, for example, in a first state. The flow of the one or more agricultural materials may be moved, for example, in a second state. The flow of the one or more agricultural materials may be stopped or moved via one or more devices, such as via one or more pumps or one or more valves. At 708, the density of the one or more agricultural materials may be determined via an agricultural materials density device (e.g., density measurement device 2020, 3010). The density of the one or more agricultural materials may be determined when the flow of the one or more agricultural materials is stopped in the first state and/or when the flow of the one or more agricultural materials is moving in the second state. A comparison of the density of the one or more agricultural materials may be determined when the flow of the one or more agricultural materials is stopped in the first state versus when the flow of the one or more agricultural materials is moving in the second state. At 710, the ratio of the at least one solid to the at least one liquid in the one or more agricultural materials may be determined. For example, the ratio of the at least one solid to the at least one liquid in the one or more agricultural materials may be determined based on the determined density of the one or more agricultural materials stopped in the first state and moving in the second state.

EXAMPLES

The following are non-limiting examples.

Example 1—A system for analyzing one or more agricultural materials comprising: one or more inlets receiving the one or more agricultural materials, the one or more agricultural materials comprising at least one solid and at least one liquid; a chamber configured to house the one or more agricultural materials, the chamber comprising a mixing device configured to mix the one or more agricultural materials; a flow control device configured to stop a flow of the one or more agricultural materials in a first state or move the flow of the one or more agricultural materials in a second state; and an agricultural materials density device configured to determine a density of the one or more agricultural materials when the flow of the one or more agricultural materials is stopped in the first state and when the flow of the one or more agricultural materials is moving in the second state.

Example 2—the system of Example 1, further comprising a processor configured to determine a ratio of the at least one solid to the at least one liquid in the one or more agricultural materials based on the determined density of the one or more agricultural materials stopped in the first state and moving in the second state.

Example 3—the system of any of Examples 1 to 2, wherein the agricultural materials density device comprises a u-tube device.

Example 4—the system of any of Examples 1 to 3, wherein the agricultural materials density device comprises a u-tube device comprising a first straight portion and a second curved portion, the first straight portion being oriented in a vertical direction.

Example 5—the system of any of Examples 1 to 4, wherein the one or more agricultural materials are one or more soil slurries.

Example 6—the system of Example 5, further comprising a measurement sub-system comprising one or more sensors and one or more ports, the one or more ports being configured to provide a fluid to clean the one or more sensors of the measurement sub-system, wherein the one or more sensors comprise at least one of an ion selective electrode sensor or an ion selective field-effect electrode sensor.

Example 7—the system of any of Examples 1 to 6, wherein the flow control device is at least one of a pump or a valve.

Example 8—the system of any of Examples 1 to 7, wherein an additional liquid is added to the one or more agricultural materials depending on the determined ratio of the at least one solid to the at least one liquid in the one or more agricultural materials.

Example 9—the system of any of Examples 1 to 8, wherein the processor is configured to determine the ratio of the at least one solid to the at least one liquid in the one or more agricultural materials based on the determined density of the at least one solid, the determined density of the one or more agricultural materials, and a density of the at least one liquid.

Example 10—A system for analyzing one or more agricultural materials comprising: one or more inlets receiving the one or more agricultural materials, the one or more agricultural materials comprising at least one solid and at least one liquid; a chamber configured to house the one or more agricultural materials, the chamber comprising a mixing device configured to mix the one or more agricultural materials; a particle density device configured to determine a density of the at least one solid of the one or more agricultural materials; and an agricultural materials density device configured to determine a density of the one or more agricultural materials comprising the at least one solid and the at least one liquid.

Example 11—the system of Example 10, further comprising a processor configured to determine, based on the determined density of the at least one solid and the determined density of the one or more agricultural materials, the ratio of the at least one solid to the at least one liquid in the one or more agricultural materials.

Example 12—the system of any of Examples 10 to 11, wherein the one or more agricultural materials are one or more soil slurries.

Example 13—the system of any of Examples 10 to 12, further comprising a measurement sub-system comprising one or more sensors and one or more ports, the one or more ports being configured to provide a fluid to clean the one or more sensors of the measurement sub-system, wherein the one or more sensors comprise at least one of an ion selective electrode sensor or an ion selective field-effect electrode sensor.

Example 14—the system of any of Examples 10 to 13, wherein an additional liquid is added to the one or more agricultural materials depending on a determined ratio of the at least one solid to the at least one liquid in the one or more agricultural materials.

Example 15—the system of any of Examples 10 to 14, wherein the agricultural materials density device comprises a u-tube device.

Example 16—the system of any of Examples 10 to 15, wherein the agricultural materials density device comprises a u-tube device comprising a first straight portion and a second curved portion, the first straight portion being oriented in a vertical direction.

Example 17—the system of Example 16, wherein the agricultural materials density device is configured to determine the density of the one or more agricultural materials when a flow of the one or more agricultural materials is stopped in a first state and when the flow of the one or more agricultural materials is moving in a second state.

Example 18—the system of any of Examples 10 to 17, wherein the processor is configured to determine the ratio of the at least one solid to the at least one liquid in the one or more agricultural materials based on the determined density of the at least one solid, the determined density of the one or more agricultural materials, and a density of the at least one liquid.

Example 19—the system of any of Examples 10 to 18, wherein the particle density device is configured to measure reflectance for the one or more agricultural materials via wavelengths in visible and infrared spectrums.

Example 20—the system of any of Examples 10 to 19, wherein the particle density device is configured to perform a sensing technique comprising determining at least one of an optical wavelength reflectance/absorption value, electromagnetic wavelength reflectance/absorption value, temperature value, electrical current flow value, electrical conductivity value, Xray fluorescence value, Laser-Induced Breakdown Spectroscopy value, Near Infrared Spectroscopy value, Mid Infrared Spectroscopy value, Far Infrared Spectroscopy value, Xray Diffraction value, Gamma Ray emission value, Raman Spectroscopy value, Multi-Spectral Sensing value, Short wave infrared value, Microfluidic value, Acoustic resonance spectroscopy value, Fourier Transform Infrared Spectroscopy value, Photoemission spectroscopy value, spectrophotometry value, thermal infrared spectroscopy value, video spectroscopy value, or hyperspectral imaging value, laser diffraction value.

Example 21—A system for analyzing one or more agricultural materials comprising: one or more inlets receiving one or more agricultural materials, the one or more agricultural materials comprising at least one solid and at least one liquid; a chamber configured to house the one or more agricultural materials, the chamber comprising a mixing device configured to mix the one or more agricultural materials; and a particle density device configured to determine a mass of organic matter of the at least one solid of the one or more agricultural materials.

Example 22—the system of Example 21, wherein the one or more agricultural materials is a soil slurry.

Example 23—the system of any of Examples 21 to 22, wherein the particle density measurement device is configured to determine the mass of the organic matter of the at least one solid of the one or more agricultural materials by measuring a reflectance of the one or more agricultural materials as the one or more agricultural materials flow past a portion of the particle density measurement device.

Example 24—the system of Example 23, wherein the particle density measurement device is configured to measure the reflectance via a sensor using multiple wavelengths in at least one of the visible or infrared spectrums.

Example 25—the system of Example 24, wherein the sensor uses sensing techniques comprising at least one of optical wavelength reflectance/absorption values, electromagnetic wavelength reflectance/absorption values, temperature, electrical current flow, electrical conductivity, Xray fluorescence, Laser-Induced Breakdown Spectroscopy, Near Infrared Spectroscopy, Mid Infrared Spectroscopy, Far Infrared Spectroscopy, Xray Diffraction, Gamma Ray emission, Raman Spectroscopy, Multi-Spectral Sensing, Short wave infrared, Microfluidics, Acoustic resonance spectroscopy, Fourier Transform Infrared Spectroscopy, Photoemission spectroscopy, spectrophotometry, thermal infrared spectroscopy, video spectroscopy, or hyperspectral imaging, laser diffraction.

Example 26—the system of any of Examples 21 to 25, wherein the particle density measurement device is configured to determine electrical conductivity of soil within the one or more agricultural materials, the electrical conductivity of the soil being used to determine nutrient information relating to the one or more agricultural materials.

Example 27—the system of any of Examples 21 to 26, wherein the particle density measurement device comprises a plurality of electrodes configured to determine an electrical conductivity of the solid within the one or more agricultural materials.

Example 28—the system of Example 27, wherein at least one of the plurality of electrodes is placed on either side of a flow of the one or more agricultural materials, each of the at least one of the plurality of electrodes being configured to measure electrical conductivity in contact with the side of the flow of the one or more agricultural materials.

Example 29—the system of Example 27, wherein the particle density measurement device is configured to determine the electrical conductivity of soil within the one or more agricultural materials via one or more sensing techniques comprising at least one of electrical current flow, electrical conductivity, electro-magnetic induction, electrical resistivity, time domain reflectometry, amplitude domain reflectometry, or frequency domain reflectometry.

Example 30—A method for analyzing one or more agricultural materials comprising: receiving the one or more agricultural materials, wherein the one or more agricultural materials comprise at least one solid and at least one liquid; housing, via a chamber comprising a mixing device configured to mix the one or more agricultural materials, the one or more agricultural materials; stopping a flow of the one or more agricultural materials in a first state or moving the flow of the one or more agricultural materials in a second state; and determining, via an agricultural materials density device, the density of the one or more agricultural materials when the flow of the one or more agricultural materials is stopped in the first state and when the flow of the one or more agricultural materials is moving in the second state.

Example 31—the method of Example 30, further comprising determining a ratio of the at least one solid to the at least one liquid in the one or more agricultural materials based on the determined density of the one or more agricultural materials stopped in the first state and moving in the second state.

Example 32—the method of any of Examples 30 to 31, wherein the agricultural materials density device comprises a u-tube device.

Example 33—the method of any of Examples 30 to 32, wherein the agricultural materials density device comprises a u-tube device comprising a first straight portion and a second curved portion, the first straight portion being oriented in a vertical direction.

Example 34—the method of any of Examples 30 to 33, wherein the one or more agricultural materials are one or more soil slurries.

Example 35—the method of Example 34, further comprising cleaning one or more sensors of a measurement sub-system, wherein the one or more sensors comprise at least one of an ion selective electrode sensor or an ion selective field-effect electrode sensor.

Example 36—the method of any of Examples 30 to 35, wherein the flow of the one or more agricultural materials is stopped or moved via at least one of a pump or a valve.

Example 37—the method of any of Examples 30 to 36, wherein an additional liquid is added to the one or more agricultural materials depending on the determined ratio of the at least one solid to the at least one liquid in the one or more agricultural materials.

Example 38—the method of any of Examples 30 to 37, further comprising determining the ratio of the at least one solid to the at least one liquid in the one or more agricultural materials based on the determined density of the at least one solid, the determined density of the one or more agricultural materials, and a density of the at least one liquid.

Example 39—A method for analyzing one or more agricultural materials comprising: receiving the one or more agricultural materials, wherein the one or more agricultural materials comprise at least one solid and at least one liquid; housing the one or more agricultural materials via a chamber comprising a mixing device configured to mix the one or more agricultural materials; determining, via a particle density device, the density of the at least one solid of the one or more agricultural materials; and determining, via an agricultural materials density device, the density of the one or more agricultural materials comprising the at least one solid and the at least one liquid.

Example 40—the method of Example 39, further comprising determining, based on the determined density of the at least one solid and the determined density of the one or more agricultural materials, the ratio of the at least one solid to the at least one liquid in the one or more agricultural materials.

Example 41—the method of any of Examples 39 to 40, wherein the one or more agricultural materials are one or more soil slurries.

Example 42—the method of Example 41, wherein the at least one liquid is water.

Example 43—the method of any of Examples 39 to 42, further comprising adding liquid to the one or more agricultural materials based on the determined ratio of the at least one solid to the at least one liquid in the one or more agricultural materials.

Example 44—the method of any of Examples 39 to 43, wherein the agricultural materials density device comprises a u-tube device.

Example 45—the method of any of Examples 39 to 44, wherein the agricultural materials density device comprises a u-tube device comprising a first straight portion and a second curved portion, the first straight portion being oriented in a vertical direction.

Example 46—the method of Example 45, further comprising determining the density of the one or more agricultural materials when a flow of the one or more agricultural materials is stopped in a first state and when the flow of the one or more agricultural materials is moving in a second state.

Example 47—the method of any of Examples 39 to 46, further comprising determining the ratio of the at least one solid to the at least one liquid in the one or more agricultural materials based on the determined density of the at least one solid, the determined density of the one or more agricultural materials, and a density of the at least one liquid.

Example 48—the method of any of Examples 39 to 47, further comprising measuring, via the particle density device, reflectance for the one or more agricultural materials via wavelengths in visible and infrared spectrums.

Example 49—the method of any of Examples 39 to 48, wherein the particle density device performs a sensing technique comprising determining at least one of an optical wavelength reflectance/absorption value, electromagnetic wavelength reflectance/absorption value, temperature value, electrical current flow value, electrical conductivity value, Xray fluorescence value, Laser-Induced Breakdown Spectroscopy value, Near Infrared Spectroscopy value, Mid Infrared Spectroscopy value, Far Infrared Spectroscopy value, Xray Diffraction value, Gamma Ray emission value, Raman Spectroscopy value, Multi-Spectral Sensing value, Short wave infrared value, Microfluidic value, Acoustic resonance spectroscopy value, Fourier Transform Infrared Spectroscopy value, Photoemission spectroscopy value, spectrophotometry value, thermal infrared spectroscopy value, video spectroscopy value, or hyperspectral imaging value, laser diffraction value.

Example 50—A method for analyzing one or more agricultural materials comprising: receiving one or more agricultural materials, wherein the one or more agricultural materials comprise at least one solid and at least one liquid; housing the one or more agricultural materials via a chamber comprising a mixing device configured to mix the one or more agricultural materials; and determining, via a particle density device, the mass of organic matter of the at least one solid of the one or more agricultural materials.

Example 51—the method of Example 50, wherein the one or more agricultural materials is a soil slurry.

Example 52—the method of any of Examples 50 to 51, further comprising determining, via the particle density measurement device, the mass of the organic matter of the at least one solid of the one or more agricultural materials by measuring a reflectance of the one or more agricultural materials as the one or more agricultural materials flow past a portion of the particle density measurement device.

Example 53—the method of Example 52, further comprising measuring, via the particle density measurement device, the reflectance via a sensor using multiple wavelengths in at least one of the visible or infrared spectrums.

Example 54—the method of Example 53, wherein the sensor uses sensing techniques comprising at least one of optical wavelength reflectance/absorption values, electromagnetic wavelength reflectance/absorption values, temperature, electrical current flow, electrical conductivity, Xray fluorescence, Laser-Induced Breakdown Spectroscopy, Near Infrared Spectroscopy, Mid Infrared Spectroscopy, Far Infrared Spectroscopy, Xray Diffraction, Gamma Ray emission, Raman Spectroscopy, Multi-Spectral Sensing, Short wave infrared, Microfluidics, Acoustic resonance spectroscopy, Fourier Transform Infrared Spectroscopy, Photoemission spectroscopy, spectrophotometry, thermal infrared spectroscopy, video spectroscopy, or hyperspectral imaging, laser diffraction.

Example 55—the method of any of Examples 50 to 54, further comprising determining, via the particle density measurement device, electrical conductivity of soil within the one or more agricultural materials, the electrical conductivity of the soil being used to determine nutrient information relating to the one or more agricultural materials.

Example 56—the method of any of Examples 50 to 55, wherein the particle density measurement device comprises a plurality of electrodes configured to determine an electrical conductivity of the solid within the one or more agricultural materials.

Example 57—the method of Example 56, wherein at least one of the plurality of electrodes is placed on either side of a flow of the one or more agricultural materials, each of the at least one of the plurality of electrodes being configured to measure electrical conductivity in contact with the side of the flow of the one or more agricultural materials.

Example 58—the method of Example 56, further comprising determining, via the particle density measurement device, the electrical conductivity of soil within the one or more agricultural materials via one or more sensing techniques comprising at least one of electrical current flow, electrical conductivity, electro-magnetic induction, electrical resistivity, time domain reflectometry, amplitude domain reflectometry, or frequency domain reflectometry.

Example 59—A system for analyzing one or more agricultural materials comprising: one or more inlets receiving one or more agricultural materials, the one or more agricultural materials comprising at least one solid and at least one liquid; a chamber configured to house the one or more agricultural materials, the chamber comprising a mixing device configured to mix the one or more agricultural materials; and a measurement device configured to determine electrical conductivity of soil within the one or more agricultural materials, the electrical conductivity of the soil being used to determine nutrient information relating to the one or more agricultural materials.

Example 60—the system of Example 59, wherein the one or more agricultural materials is a soil slurry.

Example 61—the system of Example 59 or 60, wherein the particle density measurement device comprises a plurality of electrodes configured to determine an electrical conductivity of the solid within the one or more agricultural materials.

Example 62—the system of Example 61, wherein at least one of the plurality of electrodes is placed on either side of a flow of the one or more agricultural materials, each of the at least one of the plurality of electrodes being configured to measure electrical conductivity in contact with the side of the flow of the one or more agricultural materials.

Example 63—the system of Example 61, wherein the particle density measurement device is configured to determine the electrical conductivity of soil within the one or more agricultural materials via one or more sensing techniques comprising at least one of electrical current flow, electrical conductivity, electro-magnetic induction, electrical resistivity, time domain reflectometry, amplitude domain reflectometry, or frequency domain reflectometry.

Example 64—A method for analyzing one or more agricultural materials comprising: receiving one or more agricultural materials, wherein the one or more agricultural materials comprise at least one solid and at least one liquid; housing the one or more agricultural materials via a chamber comprising a mixing device configured to mix the one or more agricultural materials; and determining, via a particle density device, the mass of organic matter of the at least one solid of the one or more agricultural materials.

Example 65—the method of Example 64, wherein the one or more agricultural materials is a soil slurry.

Example 66—the method of Example 64 or 65, wherein the particle density measurement device comprises a plurality of electrodes configured to determine an electrical conductivity of the solid within the one or more agricultural materials.

Example 67—the method of Example 66, wherein at least one of the plurality of electrodes is placed on either side of a flow of the one or more agricultural materials, each of the at least one of the plurality of electrodes being configured to measure electrical conductivity in contact with the side of the flow of the one or more agricultural materials.

Example 68—the method of Example 66, further comprising determining, via the particle density measurement device, the electrical conductivity of soil within the one or more agricultural materials via one or more sensing techniques comprising at least one of electrical current flow, electrical conductivity, electro-magnetic induction, electrical resistivity, time domain reflectometry, amplitude domain reflectometry, or frequency domain reflectometry.

Additional Example—Slurry Characteristic Determination Via Electrical Conductivity Measurement 1A. A system for analyzing one or more agricultural materials comprising: a chamber receiving an agricultural material, the agricultural material comprising a solid; the chamber comprising a mixing device configured to mix the solid with a liquid to form a slurry; and a measurement device configured to measure electrical conductivity of the solid within the slurry, the electrical conductivity of the solid being used to determine a characteristic relating to the solid within the slurry.

2A. The system of Example 1A, wherein the measurement device is a particle density measurement device configured to measure a density of the solid in the slurry via the electrical conductivity measurement.

3A. The system of Example 2A, wherein the solid is a soil sample and the liquid is water which defines a soil slurry.

4A. The system according to Example 2A or 3A, wherein the measurement device comprises an electrical conductivity sensor comprising a plurality of electrodes immersible in the slurry and configured to determine the electrical conductivity of the soil within the slurry.

5A. The system of Example 3A, wherein at least one of the plurality of electrodes is placed on each of opposing sides of a flow of the slurry in spaced relationship within a flow conduit, each of the at least one of the plurality of electrodes being configured to measure electrical conductivity in contact with a respective side of the flow of the slurry.

6A. The system according to Example 5A, wherein the flow conduit and chamber are integral fluidic parts of a closed slurry recirculation flow loop which comprises a recirculation pump configured to circulate the slurry through the flow conduit and chamber.

7A. The system according to any one of Examples 2-6A, wherein the measurement device is configured to determine the electrical conductivity of soil within the slurry via one or more sensing techniques comprising at least one of electrical current flow, electrical conductivity, electro-magnetic induction, electrical resistivity, time domain reflectometry, amplitude domain reflectometry, or frequency domain reflectometry.

8A. The system of Example 1A, wherein the characteristic relating to the solid within the slurry is useful in agriculture.

9A. The system of Example 8A, wherein the characteristic is soil nutrient information relating to the solid of the agricultural material.

10A. The system according to any one of Examples 1-9A, further comprising a system controller operably coupled to the measurement device, the system controller being configured to determine a characteristic relating to the solid within the slurry.

11A. A method for analyzing one or more agricultural materials comprising: receiving an agricultural material comprising a solid and a liquid in a chamber of a mixing device; mixing the solid and liquid to form a slurry; determining, via a measurement device, electrical conductivity of soil within slurry; and determining a characteristic relating to the solid within the slurry from the measured electrical conductivity of the soil in the slurry.

12A. The method of Example 11A, wherein the solid is a soil sample and the liquid is water which defines a soil slurry.

13A. The method of Example 12A, wherein the receiving step is preceded by a step of collecting the soil sample from an agricultural field.

14A. The method according to any one of Examples 11-13A, wherein the measurement device is a particle density measurement device configured to measure a density of the solid in the slurry via the electrical conductivity measurement.

15A. The method according to any one of Examples 11-14A, wherein the measurement device comprises an electrical conductivity sensor comprising a plurality of electrodes immersible in the slurry and configured to determine the electrical conductivity of the soil within the slurry.

16A. The method of Example 15A, wherein at least one of the plurality of electrodes is placed on each of opposing sides of a flow of the slurry in spaced relationship within a flow conduit, each of the at least one of the plurality of electrodes being configured to measure electrical conductivity in contact with a respective side of the flow of the slurry.

17A. The method according to Example 16A, wherein the flow conduit and chamber are integral fluidic parts of a closed slurry recirculation flow loop which comprises a recirculation pump configured to circulate the slurry through the flow conduit and chamber.

18A. The method according to any one of Examples 11-17A, further comprising determining, via the measurement device, the electrical conductivity of soil within the slurry via one or more sensing techniques comprising at least one of electrical current flow, electrical conductivity, electro-magnetic induction, electrical resistivity, time domain reflectometry, amplitude domain reflectometry, or frequency domain reflectometry.

19A. The method according to Example 11A, wherein the characteristic is soil nutrient information relating to the solid of the agricultural material.

20A. The method according to any one of Examples 1-9A, further comprising a system controller which performs the step of determining a characteristic relating to the solid within the slurry from the measured electrical conductivity of the soil in the slurry.

Additional Examples—Agricultural Slurry Density Measurement

1B. A system for analyzing one or more agricultural materials comprising: a chamber receiving an agricultural material, the agricultural material comprising a solid; the chamber comprising a mixing device configured to mix the solid with a liquid to form a slurry; a flow control device configured to stop a flow of the slurry with solid in a first state or move the flow of the slurry in a second state; and an agricultural materials density measurement device configured to determine the density of the solid within the slurry when the flow of the slurry is stopped in the first state, and when the flow of the slurry is moving in the second state.

2B. The system of Example 1B, further comprising a processor configured to determine a ratio of the solid to the liquid in the slurry based on the determined density of the solid when the slurry is stopped in the first state and moving in the second state.

3B. The system of any of Examples 1B to 2B, wherein the agricultural materials density measurement device comprises a U-tube device.

4B. The system of Example 3B, wherein the U-tube device comprises a first straight portion and a second curved portion in fluidly coupled to the first straight portion, the first straight portion being oriented in a vertical direction.

5B. The system of any of Examples 1B to 4B, wherein solid of the agricultural materials is soil forming a soil slurry.

6B. The system of Example 5B, further comprising a measurement sub-system comprising one or more sensors and one or more ports, the one or more ports being configured to provide a fluid to clean the one or more sensors of the measurement sub-system, wherein the one or more sensors comprise at least one of an ion selective electrode sensor or an ion selective field-effect electrode sensor.

7B. The system of any of Examples 1B to 6B, wherein the flow control device is at least one of a pump or a valve.

8B. The system of any of Examples 2B to 7B, wherein an additional amount of the liquid is added to the one or more agricultural materials depending on the determined ratio of the solid to the liquid in the slurry.

9B. The system of any of Examples 2B to 8B, wherein the processor is configured to determine the ratio of the solid to the liquid in the one or more agricultural materials based on the determined density of the solid and a density of the liquid which comprises the slurry.

10B. A method for analyzing one or more agricultural materials comprising: receiving an agricultural material comprising a solid and a liquid in a chamber of a mixing device; mixing the solid and liquid to form a slurry; stopping a flow of the slurry in a first state or moving the flow slurry in a second state; and determining, via an agricultural materials density measurement device, the density of the solid within the slurry when the flow of the slurry is stopped in the first state and when the flow of the slurry is moving in the second state.

11B. The method of Example 10B, further comprising determining a ratio of the solid to the liquid in the slurry based on the determined density of the solid when the slurry is stopped in the first state and moving in the second state.

12B. The method of any of Examples 10B to 11B, wherein the agricultural materials density measurement device comprises a U-tube device.

13B. The method of Example 12B, wherein the U-tube device comprises a first straight portion and a second curved portion fluidly coupled to the first straight portion, the first straight portion being oriented in a vertical direction.

14B. The system of any of Examples 10B to 13B, wherein solid of the agricultural materials is soil forming a soil slurry.

15B. The method of Example 14B, further comprising cleaning one or more sensors of a measurement sub-system, wherein the one or more sensors comprise at least one of an ion selective electrode sensor or an ion selective field-effect electrode sensor.

16B. The method of any of Examples 10B to 15B, wherein the flow of the slurry is stopped or moved via at least one of a pump or a valve.

17B. The method of any of Examples 11B to 16B, wherein additional liquid is added to the slurry depending on the determined ratio of the at least one solid to the at least one liquid in the one or more agricultural materials.

18B. The method of any of Examples 11B to 17B, further comprising determining the ratio of the solid to the liquid in the slurry based on the determined density of the solid and a density of the at least one liquid.

19B. The method of Example 18B, further comprising a programmable processor which determines the ration of the solid to the liquid in the slurry.

20B. The method of Example 19B, wherein the agricultural materials density measurement device is operably coupled to the processor.

Additional Examples—Slurry Solids Reflectance Measurement

1C. A system for analyzing one or more agricultural materials comprising: a chamber receiving an agricultural material, the agricultural material comprising a solid; the chamber comprising a mixing device configured to mix the solid with a liquid to form a slurry; and a particle density measurement device configured to determine a characteristic relating to the solid within the slurry by measuring a reflectance of the solid as the slurry flows past a portion of the particle density measurement device.

2C. The system of Example 1C, wherein the particle density measurement device is configured to determine a mass of the organic matter of the solid in the slurry.

3C. The system of Example 1C or 2C, wherein the particle density measurement device is configured to determine a value of the organic matter within the slurry.

4C. The system of Example 3C, wherein the particle density measurement device generates a signal which is proportional to a content of organic matter in the solid in the slurry.

5C. The system of Example 4C, wherein the signal is received by system controller configured to determine a density of the solid in the slurry based on the content of organic matter.

6C. The system according to any one of Examples 1C-5C, wherein the particle density measurement device is configured to determine a value of minerals within the slurry.

7C. The system according to any one of Examples 1C-6C, wherein the particle density measurement device is configured to measure the reflectance via a sensor using multiple wavelengths in at least one of the visible and infrared spectrums.

8C. The system of Example 7C, wherein the sensor uses sensing techniques comprising at least one of optical wavelength reflectance/absorption values, electromagnetic wavelength reflectance/absorption values, temperature, electrical current flow, electrical conductivity, Xray fluorescence, Laser-Induced Breakdown Spectroscopy, Near Infrared Spectroscopy, Mid Infrared Spectroscopy, Far Infrared Spectroscopy, Xray Diffraction, Gamma Ray emission, Raman Spectroscopy, Multi-Spectral Sensing, Short wave infrared, Microfluidics, Acoustic resonance spectroscopy, Fourier Transform Infrared Spectroscopy, Photoemission spectroscopy, spectrophotometry, thermal infrared spectroscopy, video spectroscopy, and hyperspectral imaging, laser diffraction.

9C. The system according to Example 7C or 8C, wherein the particle density measurement device comprises an inlet, an outlet, and an elongated flow channel extending therebetween which defines a flow path of the slurry through the device.

10C. The system according to Example 9C, wherein the sensor is disposed adjacent to the flow channel to measure the reflectance of the solid in the slurry as the slurry flows through the flow path.

11C. The system according to Example 10C, wherein the particle density measurement device includes a sapphire lens with a view into the flow channel through which the sensor measures the reflectance of the solid as the slurry flows along the flow path.

12C. A method for analyzing one or more agricultural materials comprising: receiving an agricultural material comprising a solid and a liquid in a chamber of a mixing device; mixing the solid and liquid to form a slurry; flowing the slurry through a particle density measurement device; and determining a characteristic relating to the solid within the slurry by measuring a reflectance from the solid as the slurry flows through the particle density measurement device.

13C. The method of Example 11C, wherein the solid is a soil sample and the liquid is water which defines a soil slurry.

14C. The method of Example 12C, wherein the receiving step is preceded by a step of collecting the soil sample from an agricultural field. determining, via a particle density device, a mass of organic matter of the at least one solid of the one or more agricultural materials.

15C. The method according to any one of Examples 12C-14C, wherein the particle density measurement device is configured to determine a mass of the organic matter of the solid in the slurry.

16C. The method according to any one of Examples 12C-15C, wherein the particle density measurement device is configured to determine a value of the organic matter within the slurry.

17C. The method according to any one of Examples 12C-16C, further comprising measuring, via the particle density measurement device, the reflectance via a sensor using multiple wavelengths in at least one of the visible or infrared spectrums.

18C. The method of Example 17C, wherein the sensor uses sensing techniques comprising at least one of optical wavelength reflectance/absorption values, electromagnetic wavelength reflectance/absorption values, temperature, electrical current flow, electrical conductivity, Xray fluorescence, Laser-Induced Breakdown Spectroscopy, Near Infrared Spectroscopy, Mid Infrared Spectroscopy, Far Infrared Spectroscopy, Xray Diffraction, Gamma Ray emission, Raman Spectroscopy, Multi-Spectral Sensing, Short wave infrared, Microfluidics, Acoustic resonance spectroscopy, Fourier Transform Infrared Spectroscopy, Photoemission spectroscopy, spectrophotometry, thermal infrared spectroscopy, video spectroscopy, or hyperspectral imaging, laser diffraction.

Additional Example—Slurry Characteristic Determination Via Electrical Conductivity Measurement 1D. A system for analyzing one or more agricultural materials comprising: a chamber receiving an agricultural material, the agricultural material comprising a solid; the chamber comprising a mixing device configured to mix the solid with a liquid to form a slurry; and a measurement device configured to measure electrical conductivity of the solid within the slurry, the electrical conductivity of the solid being used to determine a characteristic relating to the solid within the slurry.

2D. The system of Example 1D, wherein the measurement device is a particle density measurement device configured to measure a density of the solid in the slurry via the electrical conductivity measurement.

3D. The system of Example 2D, wherein the solid is a soil sample and the liquid is water which defines a soil slurry.

4D. The system according to Example 2D or 3D, wherein the measurement device comprises an electrical conductivity sensor comprising a plurality of electrodes immersible in the slurry and configured to determine the electrical conductivity of the soil within the slurry.

5D. The system of Example 3D, wherein at least one of the plurality of electrodes is placed on each of opposing sides of a flow of the slurry in spaced relationship within a flow conduit, each of the at least one of the plurality of electrodes being configured to measure electrical conductivity in contact with a respective side of the flow of the slurry.

6D. The system according to Example 5D, wherein the flow conduit and chamber are integral fluidic parts of a closed slurry recirculation flow loop which comprises a recirculation pump configured to circulate the slurry through the flow conduit and chamber.

7D. The system according to any one of Examples 2D-6D, wherein the measurement device is configured to determine the electrical conductivity of soil within the slurry via one or more sensing techniques comprising at least one of electrical current flow, electrical conductivity, electro-magnetic induction, electrical resistivity, time domain reflectometry, amplitude domain reflectometry, or frequency domain reflectometry.

8D. The system of Example 1D, wherein the characteristic relating to the solid within the slurry is useful in agriculture.

9D. The system of Example 8D, wherein the characteristic is soil nutrient information relating to the solid of the agricultural material.

10D. The system according to any one of Examples 1D-9D, further comprising a system controller operably coupled to the measurement device, the system controller being configured to determine a characteristic relating to the solid within the slurry.

11D. A method for analyzing one or more agricultural materials comprising: receiving an agricultural material comprising a solid and a liquid in a chamber of a mixing device; mixing the solid and liquid to form a slurry; determining, via a measurement device, electrical conductivity of soil within slurry; and determining a characteristic relating to the solid within the slurry from the measured electrical conductivity of the solid in the slurry.

12D. The method of Example 11D, wherein the solid is a soil sample and the liquid is water which defines a soil slurry.

13D. The method of Example 12D, wherein the receiving step is preceded by a step of collecting the soil sample from an agricultural field.

14D. The method according to any one of Examples 11D-13D, wherein the measurement device is a particle density measurement device configured to measure a density of the solid in the slurry via the electrical conductivity measurement.

15D. The method according to any one of Examples 11D-14D, wherein the measurement device comprises an electrical conductivity sensor comprising a plurality of electrodes immersible in the slurry and configured to determine the electrical conductivity of the soil within the slurry.

16D. The method of Example 15D, wherein at least one of the plurality of electrodes is placed on each of opposing sides of a flow of the slurry in spaced relationship within a flow conduit, each of the at least one of the plurality of electrodes being configured to measure electrical conductivity in contact with a respective side of the flow of the slurry.

17D. The method according to Example 16D, wherein the flow conduit and chamber are integral fluidic parts of a closed slurry recirculation flow loop which comprises a recirculation pump configured to circulate the slurry through the flow conduit and chamber.

18D. The method according to any one of Examples 11D-17D, further comprising determining, via the measurement device, the electrical conductivity of soil within the slurry via one or more sensing techniques comprising at least one of electrical current flow, electrical conductivity, electro-magnetic induction, electrical resistivity, time domain reflectometry, amplitude domain reflectometry, or frequency domain reflectometry.

19D. The method according to Example 11D, wherein the characteristic is soil nutrient information relating to the solid of the agricultural material.

20D. The method according to any one of Examples 1D-9D, further comprising a system controller which performs the step of determining a characteristic relating to the solid within the slurry from the measured electrical conductivity of the soil in the slurry.

While the inventions have been described with respect to specific examples including presently preferred modes of carrying out the inventions, those skilled in the art will appreciate that there are numerous variations and permutations of the above described systems and techniques. It is to be understood that other embodiments may be utilized and structural and functional modifications may be made without departing from the scope of the present inventions. Thus, the spirit and scope of the inventions should be construed broadly as set forth in the appended claims.

What is claimed is:

1. A system for analyzing one or more agricultural materials comprising: a chamber receiving an agricultural material, the agricultural material comprising a solid; the chamber comprising a mixing device configured to mix the solid with a liquid to form a slurry; and a measurement device configured to measure electrical conductivity of the solid within the slurry, the electrical conductivity of the solid being used to determine a characteristic relating to the solid within the slurry, wherein the measurement device is a particle density measurement device configured to measure a density of the solid in the slurry via the electrical conductivity measurement wherein the solid is a soil sample and the liquid is water which defines a soil slurry: wherein at least one of a plurality of electrodes is placed on opposing sides of a flow of the slurry in spaced relationship within a flow conduit, each of the at least one of the plurality of electrodes being configured to measure electrical conductivity in contact with a respective side of the flow of the slurry: and wherein the flow conduit and chamber are integral fluidic parts of a closed slurry recirculation flow loop which comprises a recirculation pump configured to circulate the slurry through the flow conduit and chamber.

2. The system according to claim 1, wherein the measurement device comprises an electrical conductivity sensor comprising the plurality of electrodes immersible in the slurry and configured to determine the electrical conductivity of the soil within the slurry.

3. The system according to claim 1, wherein the measurement device is configured to determine the electrical conductivity of soil within the slurry via one or more sensing techniques comprising at least one of electrical current flow, electrical conductivity, electro-magnetic induction, electrical resistivity, time domain reflectometry, amplitude domain reflectometry, or frequency domain reflectometry.

4. The system of claim 1, wherein the characteristic relating to the solid within the slurry is useful in agriculture.

5. The system of claim 4, wherein the characteristic is soil nutrient information relating to the solid of the agricultural material.

6. The system according to claim 1, further comprising a system controller operably coupled to the measurement device, the system controller being configured to determine a characteristic relating to the solid within the slurry.

7. A method for analyzing one or more agricultural materials comprising: receiving an agricultural material comprising a solid and a liquid in a chamber of a mixing device; mixing the solid and liquid to form a slurry; determining, via a measurement device, electrical conductivity of soil within slurry; and determining a characteristic relating to the solid within the slurry from the measured electrical conductivity of the solid in the slurry, wherein the measurement device comprises an electrical conductivity sensor comprising a plurality of electrodes immersible in the slurry and configured to determine the electrical conductivity of the soil within the slurry; wherein at least one of the plurality of electrodes is placed on opposing sides of a flow of the slurry in spaced relationship within a flow conduit, each of the at least one of the plurality of electrodes being configured to measure electrical conductivity in contact with a respective side of the flow of the slurry; and wherein the flow conduit and chamber are integral fluidic parts of a closed slurry recirculation flow loop which comprises a recirculation pump configured to circulate the slurry through the flow conduit and chamber.

8. The method of claim 7, wherein the solid is a soil sample and the liquid is water which defines a soil slurry.

9. The method of claim 8, wherein the receiving step is preceded by a step of collecting the soil sample from an agricultural field.

10. The method according to claim 7, wherein the measurement device is a particle density measurement device configured to measure a density of the solid in the slurry via the electrical conductivity measurement.

11. The method according to claim 7, further comprising determining, via the measurement device, the electrical conductivity of soil within the slurry via one or more sensing techniques comprising at least one of electrical current flow, electrical conductivity, electro-magnetic induction, electrical resistivity, time domain reflectometry, amplitude domain reflectometry, or frequency domain reflectometry.

12. The method according to claim 7, wherein the characteristic is soil nutrient information relating to the solid of the agricultural material.

13. The method according to claim 7, further comprising a system controller which performs the step of determining a characteristic relating to the solid within the slurry from the measured electrical conductivity of the soil in the slurry.

\* \* \* \* \*